United States Patent [19]

Kluge et al.

[11] Patent Number: 4,499,100
[45] Date of Patent: Feb. 12, 1985

[54] BENZODIOXANYL-HYDROXYETHYLENEAMINO-PIPERIDINYL ACETANILIDES, KETONES, ESTERS AND CARBAMATES WHICH EFFECT IMMUNITY AND CALCIUM ENTRY AND β-BLOCKADE

[75] Inventors: Arthur F. Kluge, Los Altos; Robin D. Clark, Palo Alto, both of Calif.

[73] Assignee: Syntex (U.S.A.) Inc., Palo Alto, Calif.

[21] Appl. No.: 495,902

[22] Filed: May 18, 1983

[51] Int. Cl.³ .................. A61K 31/445; C07D 405/12
[52] U.S. Cl. ..................................... 514/321; 546/197; 514/825; 514/821
[58] Field of Search ............... 546/197; 542/430, 439; 424/267

[56] References Cited

U.S. PATENT DOCUMENTS

| | | | |
|---|---|---|---|
| 3,124,586 | 3/1964 | Zenitz | 546/221 |
| 3,125,574 | 5/1964 | Jansen | 544/130 |
| 3,350,403 | 10/1967 | Biel et al. | 546/197 X |
| 3,829,441 | 8/1974 | Gardner | 549/366 |
| 3,879,401 | 4/1975 | Archibald et al. | 546/190 |
| 3,944,549 | 3/1976 | Lafon | 544/295 |
| 3,992,389 | 11/1976 | Cavella et al. | 546/224 |
| 4,187,313 | 2/1980 | Gschwend et al. | 424/278 |
| 4,212,808 | 7/1980 | Gschwend et al. | 549/362 |
| 4,261,907 | 4/1981 | Gschwend et al. | 549/556 |
| 4,309,349 | 1/1982 | Gschwend et al. | 549/435 |
| 4,353,901 | 10/1982 | Clark | 424/248.57 |

FOREIGN PATENT DOCUMENTS

| | | |
|---|---|---|
| 25111 | 3/1981 | European Pat. Off. |
| 2267104 | 11/1975 | France |
| 2456738 | 12/1980 | France |
| 2057433 | 4/1981 | United Kingdom |
| 2067562 | 7/1981 | United Kingdom |

OTHER PUBLICATIONS

L. Stankeviciene et al., *Mater. Mezhvug. Nauchev. Konf. Kaunos. Med. Inst.* 25th (1976), publ., 1977, pp. 322-323 [Chem. Abst. 90, 54907c (1979)].

R. Howe et al., *J. Med. Chem.* vol. 13, (No. 2), pp. 169-176 (Mar. 1970).

*Primary Examiner*—Richard A. Schwartz
*Attorney, Agent, or Firm*—Alan M. Krubiner; Tom M. Moran; Grant D. Green

[57] ABSTRACT

Novel compounds of the general formula:

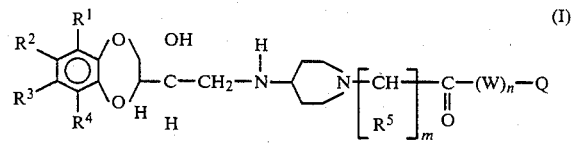

and the pharmaceutically acceptable acid addition salts thereof, wherein:

$R^1$, $R^2$, $R^3$ and $R^4$ are each independently hydrogen, lower alkyl, lower alkoxy, trifluoromethyl, halo, lower alkylthio, lower alkyl sulfinyl or lower alkyl sulfonyl;

$R^5$ is hydrogen or lower alkyl;

m is 0 or 1;

W is alkylene, —CH=CH—, —O—, or —N($R^6$)—, where $R^6$ is lower alkyl or hydrogen;

n is 0 or 1; and

Q is lower alkyl, cycloalkyl or optionally substituted phenyl.

These compounds combine β-blockade and calcium entry blockade properties in the same compound and therefore are useful in therapy in the treatment of cardiovascular diseases, including myocardial infarction, hypertension, arrhythmia and variant and exercise induced angina. The compounds are also useful in immunosuppressant therapy for immune diseases, such as rheumatoid arthritis.

49 Claims, No Drawings

BENZODIOXANYL-HYDROXYE-THYLENEAMINO-PIPERIDINYL ACETANILIDES, KETONES, ESTERS AND CARBAMATES WHICH EFFECT IMMUNITY AND CALCIUM ENTRY AND β-BLOCKADE

BACKGROUND OF THE INVENTION

The present invention is concerned with compounds, compositions, and methods useful for treating diseases in human beings which are (1) immunity disorders and also (2) those which are affected by β-blockade and calcium entry blockade. In particular, compounds wherein 4-amino piperidine is bound through the 4-amino nitrogen to a benzodioxanyl moiety by a hydroxyethylene linkage, and through the ring nitrogen to an acetanilide, ketone, ester or carbamoyl (—C(=O)—N—) residue are useful in this regard.

Large numbers of compounds are known which affect various physiological systems related to immunity and adrenergic control. Compounds which are related to the compounds of the present invention are disclosed in Belgian Pat. No. 806,380 (U.S. Pat. No. 3,944,549), and include 1-(1,4-benzodioxan-2-ylmethyl)-4-(2,6-dimethylphenylacetanilido)piperidine; in L. Stankeviciene, et al. in *Mater. Mezhvug. Nauchv. Konf. Kaunos. Med. Inst.*, 25th (1976), published in 1977, pages 322-3 [*Chem. Abstr.*, 90, 54907c (1979)]; and French Pat. No. 2,267,104. Additional references of interest in this art include U.S. Pat. Nos. 3,125,574; 3,360,529; 3,829,441; 3,879,401; 3,992,389; and 4,353,901, all of which are incorporated herein by reference. β-Adrenoreceptor blocking compounds and calcium entry blocking compounds have been used separately and in combination to mediate the symptoms of cardiovascular diseases, such as myocardial infarction, hypertension, angina and arrhythmia.

The present invention concerns a group of compounds which combine the effects of β- and calcium entry blockade in a single compound, and therefore are useful in the treatment of these cardiovascular diseases. These compounds are also used in the treatment of vasospastic disorders and as afterload reducers in the treatment of congestive heart failure. These compounds are also useful as immunosuppressants. In particular, they are useful in treating autoimmune diseases, such as rheumatoid arthritis.

SUMMARY OF THE INVENTION

In one aspect this invention concerns piperidine derivatives of the general formula:

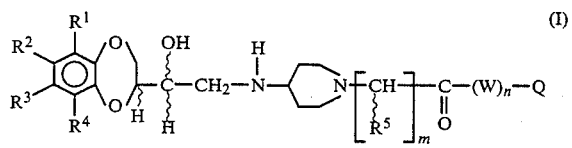

and the pharmaceutically acceptable acid addition salts thereof, wherein:
$R^1$, $R^2$, $R^3$ and $R^4$ are each independently hydrogen, lower alkyl, lower alkoxy, trifluoromethyl, halo, lower alkylthio, lower alkyl sulfinyl or lower alkyl sulfonyl;
$R^5$ is hydrogen or lower alkyl;
m is 0 or 1;
W is alkylene; —CH=CH—, —O—, or —N($R^6$)—, where $R^6$ is lower alkyl or hydrogen;
n is 0 or 1; and
Q is lower alkyl, cycloalkyl or optionally substituted phenyl.

These compounds have been shown to block β-receptors in anesthetized dogs, hence in two other aspects the invention concerns a method for affecting physiological phenomena related to β-control using the compounds of formula I, and compositions for this purpose containing these compounds. The compounds are also useful in treatment of autoimmune diseases such as rheumatoid arthritis.

Another aspect of this invention is a process for the preparation of compounds of formula I, as described in more detail hereinafter.

DETAILED DESCRIPTION OF THE INVENTION

Definitions

As used herein:

"Alkylene" refers to those hydrocarbon groups which are difunctional, containing from 1 to 4 carbon atoms, such as methylene (—CH$_2$—), ethylene (—CH$_2$CH$_2$—), propylene (—CH$_2$CH$_2$CH$_2$—), butylene (—CH$_2$CH$_2$CH$_2$CH$_2$—) and the like.

"Cycloalkyl" refers to the cycloalkyl groups containing from 3 to 8 carbon atoms, including for example, cyclopropyl, cyclobutyl, cyclopentyl, methyl cyclopentyl, cyclohexyl, cycloheptyl, cyclooctyl and the like.

"Halo" or "halogen" refers to fluoro, chloro, bromo or iodo, usually regarding halo or halogen substitution for a hydrogen atom in an organic compound.

"Isomerism" refers to compounds having the same atomic mass and atomic number but differing in one or more physical or chemical properties. Various types of isomerism include the following:

"Stereoisomer" refers to a chemical compound having the same molecular weight, chemical composition, and constitution as another, but with the atoms grouped differently. That is, certain identical chemical moieties are at different orientations in space and, therefore, when pure, has the ability to rotate the plane of polarized light. However, some pure stereoisomers may have an optical rotation that is so slight that it is undetectable with present instrumentation.

"Optical isomerism" describes one type of stereoisomerism which manifests itself by the rotation that the isomer, either pure or in solution, imparts to the plane of polarized light. It is caused in many instances by the attachment of four different chemical atoms or groups to at least one of the carbon atoms in a molecule. These isomers may be described as d-, l-, or a d,l-pair; or D-, L- or a D,L-pair; or R-, S-, or an R,S-pair, depending upon the nomenclature system employed.

"Diastereoisomer" refers to stereoisomers some or all of which are dissymmetric but which are not mirror images of each other. Diastereoisomers corresponding to a given structural formula must have at least two asymmetric atoms. A compound having two asymmetric atoms will usually exist in four diastereoisomeric forms, i.e. (−)-erythro, (+)-erythro, (−)-threo and (+)-threo.

"Geometric isomer" refers to the cis-trans isomerism that may exist in a compound containing a rigid carbon-carbon double bond; i.e.,

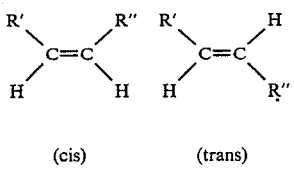

(cis)   (trans)

where R' and R" are each, for example chloro. The cis isomer describes the compound where two large groups (i.e., R' and R") are on the same side of each of the carbon atoms of the rigid double bond and the trans isomer describes the compound where two large groups (i.e., R' and R") are on opposite sides of each of the carbon atoms of the double bond. When a carbon-carbon double bond is present in a structure, each pure isomer and mixtures thereof are contemplated in the present invention.

Certain compounds of formula I wherein $R^5$ is hydrogen will have only two asymmetric carbon atoms, i.e. carbon atom 2 of the benzodioxanyl moiety and its adjacent non-cyclic carbon atom to which the hydroxyl group is attached. These compounds will exist in four stereochemical forms; i.e., (+)-erythro, (−)-erythro, (+)-threo and (−)-threo and mixtures thereof. Compounds of formula I where $R^5$ is a group other than hydrogen will have three asymmetric carbon atoms, i.e. carbon atom at the 2 position of the benzodioxanyl moiety, its adjacent noncyclic carbon atom and the carbon atom to which $R^5$ is attached. These compounds may exist in eight stereochemical forms and mixtures thereof. This application and the claims appended thereto are to be interpreted to include all possible individual stereoisomers as well as the mixtures thereof.

"Lower alkyl" refers to a branched or unbranched saturated hydrocarbon chain of 1–4 carbons, such as, for example, methyl, ethyl, n-propyl, i-propyl, n-butyl, i-butyl, s-butyl, and t-butyl.

"Lower alkoxy" refers to a group —OR wherein R is lower alkyl as herein defined.

"Lower alkylthio" refers to a group —SR wherein R is lower alkyl as herein defined.

"Lower alkyl sulfinyl" refers to

wherein R is lower alkyl as herein defined.

"Lower alkyl sulfonyl" refers to

wherein R is lower alkyl as herein defined.

"Optional" or "optionally" means that the subsequently described event or circumstance may or may not occur, and that the description includes instances where said event or circumstance occurs and instances in which it does not. For example, "optionally substituted phenyl", as depicted below, means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

"Phenyl" refers to the unsubstituted or optionally substituted unsaturated six-membered carbon ring. It is described in more detail herein below as Ar.

"Piperidine" or "piperidino-" refers to a structure having a saturated six-membered nitrogen substituted heterocyclic moiety:

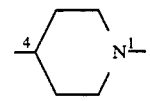

"Structure of formula I" refers to the generic structure of the compounds of the invention. The chemical bonds indicated as (⌇) in formula I indicate the nonspecific stereochemistry of the asymmetric carbon atoms, e.g. at position 2 of the benzodioxanyl ring, the adjacent carbon to which is attached the hydroxyl (—OH) group, and the carbon to which $R^5$ is attached between the piperidine ring and the carbonyl group.

In the Reaction Sequences as discussed hereinbelow:

"Ar" represents an "optionally substituted phenyl" group wherein $R^7$ to $R^{11}$ are independently defined as $R^1$ hereinabove, aminosulfonyl, hydroxyl and where $R^8$ and $R^9$ together form a —OCH$_2$O— linkage. The numbered positions are shown below:

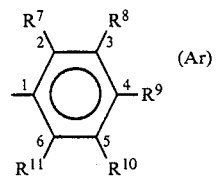

"Bzd" represents the benzodioxanyl moiety which may optionally be substituted by $R^1$ to $R^4$ as defined hereinabove. The linkage to other parts of the molecule is through the carbon atom at the 2 position and the other numbered positions of the benzodioxanyl group are indicated, as shown:

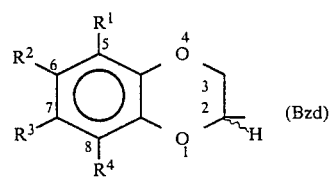

The compounds of the present invention are generally named according to the IUPAC nomenclature system. The locants for the substituents on the ring system of the above compounds of the instant invention are as depicted in the Summary of the Invention above. For example, when $R^1$ to $R^5$ are hydrogen, m is 1, W is —N($R^6$)—, where $R^6$ is hydrogen, n is 1, and Q is 2,6-dimethylphenyl, the compound of formula I is named 4-{[2-(1,4-benzodioxan-2-yl)-2-hydroxyethyl]amino}-1-[(2,6-dimethylphenyl)aminocarbonylmethyl]piperidine, and is shown below:

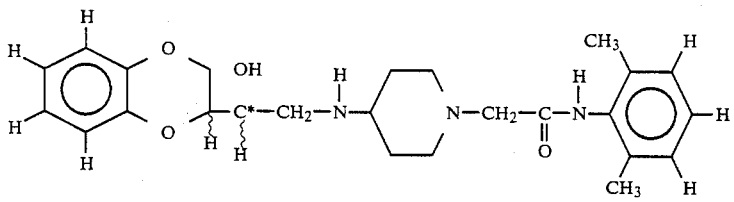 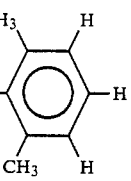

where * denotes a center of symmetry. This compound may also be named as 4-{[2-(1,4-benzodioxan-2-yl)-2-hydroxyethyl]amino}-1-(2,6-dimethylphenylcarbamoylmethyl)piperidine; or 4-{[2-(1,4-benzodioxan-2-yl)-2-hydroxyethyl]amino}-1-(2,6-dimethylacetanilido)-piperidine. For purposes of this patent application, the IUPAC designation first described above will be used.

In a similar manner when $R^1$ to $R^4$ are hydrogen, m is 0, W is —CH=CH— and Q is phenyl (Ar) wherein $R^7$ and $R^{11}$ are hydrogen and $R^8$, $R^9$ and $R^{10}$ are each methoxy, the compound of formula I is named 4-{[2-(1,4-benzodioxan-2-yl)-2-hydroxyethyl]amino}-1-[3-(3,4,5-trimethoxyphenyl)propenoyl]piperidine, and is shown below

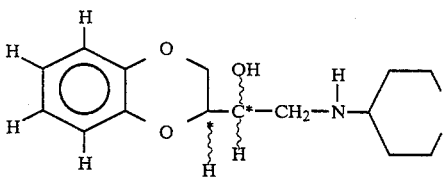 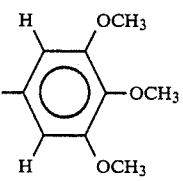

where the * denotes a center of asymmetry. This compound may also be named as 4-{[2-(1,4-benzodioxan-2-yl)-2-hydroxyethyl]amino}-1-[3,4,5-trimethoxycinnamoyl]piperidine. For the purposes of this patent application the IUPAC designation first described will be used.

In a similar manner when $R^1$ to $R^4$ are hydrogen, m is 0, W is —NH—, and Q is phenyl (Ar) wherein $R^7$ to $R^{11}$ are hydrogen, the compound of formula I is named 4-{[2-(1,4-benzodioxan-2-yl)-2-hydroxyethyl]amino}-1-[phenylaminocarbonyl]piperidine, and is shown below

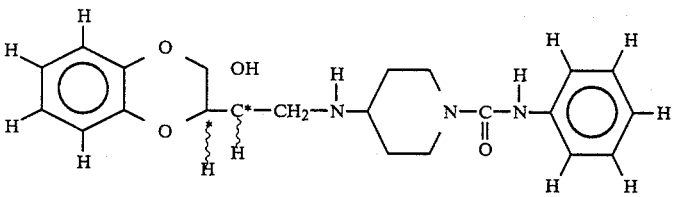 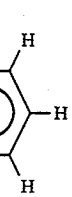

where the * denotes a center of asymmetry. The compound may also be named as 4-{[2-(1,4-benzodioxan-2-yl)-2-hydroxyethyl]amino}-1-(phenylcarbamoyl)piperidine. For the purposes of this patent application, the IUPAC designation first described will be used.

The optically active compounds herein can be designated by a number of conventions; i.e., the R- and S-sequencing rules of Cahn and Prelog; erythro and threo isomers; D- and L-isomers; d- and l-isomers; and (+) and (−)-isomers, which indicates the direction a plane of polarized light is rotated by the chemical structure, either pure or in solution. These conventions are well-known in the art and are described in detail by E. L. Eliel in *Stereochemistry of Carbon Compounds*, published by McGraw Hill Book Company, Inc. of New York in 1962 and references cited therein.

DETAILED DESCRIPTION AND PRESENTLY PREFERRED EMBODIMENTS

Embodiments of the present invention include those compounds of formula I wherein $R^1$, $R^2$, $R^3$ or $R^4$ are each independently methyl or hydrogen.

Embodiments of the present invention include those compounds of formula I wherein $R^1$, $R^2$, $R^3$ or $R^4$ are each independently methoxy or hydrogen.

Embodiments of the present invention include those compounds of formula I wherein $R^1$, $R^2$, $R^3$ or $R^4$ are each independently methylthio or hydrogen.

Embodiments of the present invention include those individual compounds of formula I wherein $R^1$, $R^2$, $R^3$ or $R^4$ are each independently chloro, bromo, fluoro or hydrogen.

Embodiments of the present invention include those compounds of formula I whenever $R^5$ is hydrogen and m is 1. A preferred subgroup of compounds are those wherein n is 1, particularly when W is —N($R^6$)— where $R^6$ is hydrogen. Another preferred subgroup are those compounds wherein Q is substituted phenyl (Ar), particularly wherein any two of the $R^7$ to $R^{11}$ substituents are independently methyl, thus producing the corresponding dimethylaniline derivatives.

A presently preferred subgroup of the above embodiments are those compounds of formula I wherein a maximum of two non-hydrogen substituents are selected from $R^1$ to $R^4$.

Embodiments of the present invention include those individual compounds of formula I wherein $R^1$ to $R^5$ are each hydrogen, m is 1, W is —$N(R^6)$— where $R^6$ is hydrogen, and Q is phenyl optionally substituted by chloro, bromo, fluoro or hydrogen.

Embodiments of the present invention are those compounds wherein $R^1$, $R^2$, $R^3$ and $R^4$ are each hydrogen. Particularly preferred compounds of this sub-group are those wherein $R^1$ to $R^5$ are all hydrogen. Other present embodiments are those compounds wherein m is 1 and $R^5$ is hydrogen.

Preferred embodiments include those compounds wherein m is 1, $R^5$ is hydrogen, n is 1, $R^6$ is hydrogen and Q is optionally substituted phenyl having three hydrogen substituents are the compounds selected from the group comprising:

4-{[2-(1,4-benzodioxan-2-yl)-2-hydroxyethyl]amino}-1-[(2,6-dimethylphenyl)aminocarbonylmethyl]piperidine;

4-{[2-(1,4-benzodioxan-2-yl)-2-hydroxyethyl]amino}-1-[(3,4-methylenedioxyphenyl)aminocarbonylmethyl]piperidine; and 4-{[2-(1,4-benzodioxan-2-yl)-2-hydroxyethyl]amino}-1-[(2,6-dichlorophenyl)aminocarbonylmethyl]piperidine.

Also presently preferred are those compounds wherein m is 1, $R^5$ is hydrogen, n is 1, W is —$N(R^6)$— where $R^6$ is hydrogen, and Q is optionally substituted phenyl having a four hydrogen substituents are the compounds selected from the group comprising:

4-{[2-(1,4-benzodioxan-2-yl)-2-hydroxyethyl]amino}-1-[(3-methylphenyl)aminocarbonylmethyl]piperidine;

4-{[2-(1,4-benzodioxan-2-yl)-2-hydroxyethyl]amino}-1-[(4-methylphenyl)aminocarbonylmethyl]piperidine;

4-{[2-(1,4-benzodioxan-2-yl)-2-hydroxyethyl]amino}-1-[(4-n-butylphenyl)aminocarbonylmethyl]piperidine;

4-{[2-(1,4-benzodioxan-2-yl)-2-hydroxyethyl]amino}-1-[(4-fluorophenyl)aminocarbonylmethyl]piperidine;

4-{[2-(1,4-benzodioxan-2-yl)-2-hydroxyethyl]amino}-1-[(4-chlorophenyl)aminocarbonylmethyl]piperidine;

4-{[2-(1,4-benzodioxan-2-yl)-2-hydroxyethyl]amino}-1-[(3-trifluoromethylphenyl)aminocarbonylmethyl]piperidine; and 4-{[2-(1,4-benzodioxan-2-yl)-2-hydroxyethyl]amino}-1-[(4-trifluoromethylphenyl)aminocarbonylmethyl]piperidine;

4-{[2-(1,4-benzodioxan-2-yl)-2-hydroxyethyl]amino}-1-[(4-methoxyphenyl)aminocarbonylmethyl]piperidine.

4-{[2-(1,4-benzodioxan-2-yl)-2-hydroxyethyl]amino}-1-[(4-hydroxyphenyl)aminocarbonylmethyl]piperidine;

4-{[2-(1,4-benzodioxan-2-yl)-2-hydroxyethyl]amino}-1-[(4-n-butylthiophenyl)aminocarbonylmethyl]piperidine;

4-{[2-(1,4-benzodioxan-2-yl)-2-hydroxyethyl]amino}-1-[(4-hydroxyphenyl)aminocarbonylmethyl]piperidine;

4-{[2-(1,4-benzodioxan-2-yl)-2-hydroxyethyl]amino}-1-[(4-aminosulfonylphenyl)aminocarbonylmethyl]piperidine; or 4-{[2-(1,4-benzodioxan-2-yl)-2-hydroxyethyl]amino}-1-[phenylaminocarbonylmethyl]piperidine.

Embodiments of the present invention include those individual compounds of formula I wherein m is 0, n is 1, W is —$N(R^6)$—, where $R^6$ is hydrogen, and Q is lower alkyl, cycloalkyl or optionally substituted phenyl. Presently preferred compounds of this subgroup include:

4-{[2-(1,4-benzodioxan-2-yl)-2-hydroxyethyl]amino}-1-[phenylaminocarbonyl]piperidine;

4-{[2-(1,4-benzodioxan-2-yl)-2-hydroxyethyl]amino}-1-[isopropylaminocarbonyl]piperidine; or 4-{[2-(1,4-benzodioxan-2-yl)-2-hydroxyethyl]amino}-1-[cyclohexylaminocarbonyl]piperidine.

Embodiments of the present invention include those individual compounds of formula I wherein m is 0, n is 1, W is —CH=CH—, and Q is lower alkyl, cycloalkyl or optionally substituted phenyl; e.g., 4-{[2-(1,4-benzodioxan-2-yl)-2-hydroxyethyl]amino}-1-[3-(3,4,5-trimethoxyphenyl)propenoyl]piperidine; or 4-{[2-(1,4-benzodioxan-2-yl)-2-hydroxyethyl]amino}-1-[3-(cyclohexyl)propenoyl]piperidine;

Embodiments of the present invention include those individual compounds of formula I wherein m is 0, n is 1, W is —O—, and Q is lower alkyl, cycloalkyl or optionally substituted phenyl.

Embodiments of the present invention include those compounds of formula I wherein m and n are each 0 1 and Q is lower alkyl, cycloalkyl or optionally substituted phenyl. Presently preferred compounds of this subgroup include:

4-{[2-(1,4-benzodioxan-2-yl)-2-hydroxyethyl]amino}-1-[benzoyl]piperidine;

4-{[2-(1,4-benzodioxan-2-yl)-2-hydroxyethyl]amino}-1-[4-fluorobenzoyl]piperidine;

4-{[2-(1,4-benzodioxan-2-yl)-2-hydroxyethyl]amino}-1-[3,4-methylenedioxybenzoyl]piperidine; or 4-{[2-(1,4-benzodioxan-2-yl)-2-hydroxyethyl]amino}-1-[methylcarbonyl]piperidine.

An additional set of present embodiments are those compounds wherein $R^5$ and $R^6$ are hydrogen or methyl; e.g., 4-{[2-(1,4-benzodioxan-2-yl)-2-hydroxyethyl]amino}-1-[(2,6-dimethylphenyl)aminocarbonyl-1-ethyl]piperidine.

The above embodiments include all possible combinations of the individual erythro and threo isomers and mixtures thereof, the individual optical isomers (i.e., d- and l-) and mixtures thereof, and the individual cis and trans isomers and mixtures thereof, and the individual mono- and disubstituted pharmaceutically acceptable acid addition salts, particularly the mono- and dihydrochloride salts, and mixtures thereof.

PROCESS FOR PREPARATION

Reaction Sequence(s) 1, 2, 2A, 3, 4, 4A, and 5 shown below, are complementary processes for linking the two "halves" of the compounds of formula I through the piperidine ring.

In the Reaction Sequence(s) below, X represents a leaving group such as, for example, halo, sulfonyl ester, preferably a halo group. The starting materials for these reaction sequence(s) are obtained as described below.

REACTION SEQUENCE 1

[where m is 1, W is —N(R⁶)—, n is 1 and Q is Ar]

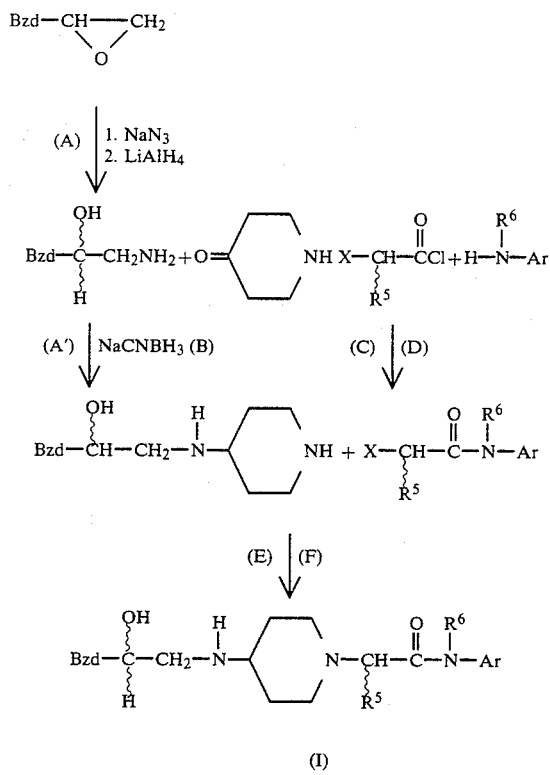

Reaction Sequence 1

The compound of formula A wherein Bzd is as described above is obtained by reacting the corresponding 2-(1,4-benzodioxan-2-yl)-1,2-dihydroxyethane with methanesulfonyl chloride or toluenesulfonyl chloride and pyridine followed by treatment with sodium hydroxide, as is well known to those in the art [see, for example, Kluge et al., *J. Med. Chem.* 24, 1320 ff (1981)].

The intermediate 1,4-benzodioxan-2-yl-2-epoxide compounds (formula A) are also prepared by condensing unsubstituted or substituted catechol with 2,3-bishalomethyloxirane in the presence of a strong base, such as alkali metal hydroxides, alkoxides or hydrides, for example, sodium or potassium hydroxide, methoxide or hydride. The reaction is run in an inert solvent such as dimethylformamide, dimethylsulfoxide and the like at a temperature of about room temperature to about 100° C., preferably from about 50° to 70° C.

The catechols (or 1,2-benzenediols) are readily available or if not readily available may be prepared by methods well known in the art. The alkylthio-, alkylsulfinyl- and alkylsulfonyl-benzodioxan-2-yl compounds are prepared in a manner similar to those described below for the corresponding substituted anilines.

1,4-Dihalo-2,3-epoxybutane is conveniently obtained by epoxidizing the corresponding olefin, e.g., dihalides of 1,4-but-2-enediols. The butene compound may be epoxidized with peracids such as perbenzoic acid, peracetic acid and the like or by catalytic epoxidation using air or oxygen with a catalyst such as a silver, platinum or palladium catalyst.

When certain aryl substituted catechols are used to prepare substituted 1,4-benzodioxan-2-yl epoxides, some uncertainty may result concerning the position of the substituents on the aryl ring of the compound of formula A. When the catechol is symmetrically substituted with identical substituents, no uncertainty will exist; e.g., tetrabromocatechol, 4,5-dimethylcatechol or 3,6-dichlorocatechol, in the substituted 1,4-benzodioxan-2-yl epoxide. If, however, the catechol is unsymmetrically substituted, e.g., 4-methylcatechol, the resulting compound will be a mixture of the 6-methyl and 7-methyl isomers of 2-(1,4-benzodioxan-2-yl)-2-epoxide. If desired, these mixtures of isomers may be separated into the individual isomers using standard separation techniques, known in the art such as fractional distillation, fractional crystallization, chromatography and the like. The invention described herein encompasses the pure isomers and mixtures of these positional isomers in the compounds of formula I, the pharmaceutically acceptable salts and the therapeutic uses thereof.

The intermediate 2-(1,4-benzodioxan-2-yl)-2-epoxide compounds may also be prepared by condensing unsubstituted or substituted salicylaldehydes or 2-hydroxyacetophenones with a 1,4-dihalo-2-butene in the presence of bases such as alkali metal hydroxides, e.g., sodium hydroxide or potassium hydroxide, or an alkali metal carbonate, e.g., sodium carbonate or potassium carbonate, in solvents such as water or ethanol. The 4-chloro-2-butenylether thus formed is reacted with a peracid such as meta-chloroperoxybenzoic acid in a solvent such as chloroform or methylene chloride at temperatures of 40° C. to 60° C. Treatment of the resulting product with an alkali metal hydroxide in a solvent mixture such as methanol/water affords the unsubstituted or substituted 1,4-benzodioxan-2-yl-2-epoxide.

The preparation of the d,l-erythro or 2-[(2S*)-oxiranyl]-1,4-(2R*)-benzodioxan and the d,l-threo or 2-[(2R*)-2-oxiranyl]-1,4-(2R*)-benzodioxan is described by Gschwend et al. in U.S. Pat. Nos. 4,187,313; 4,212,808; 4,261,907 and 4,309,349, which are incorporated herein by reference.

These compounds of formula A can then be converted to the compounds of formula A' in Reaction Sequence 1 by reacting the resulting 2-(1,4-benzodioxan-2-yl)-2-epoxide derivatives with sodium azide by heating in a solvent that will dissolve both reactants using methods known to those in the art, e.g.,; L. F. Fieser and M. Fieser, *Reagents for Organic Synthesis*, John Wiley and Sons, Inc., New York, 1967, pp. 1041–1044 and references cited therein. The intermediate hydroxy-azide produced need not be isolated and is reduced to the [2-(1,4-benzodioxan-2-yl)-2-hydroxyethyl]amine using a suitable reducing agent such as lithium aluminum hydride or hydrogen using palladium-on-carbon catalyst by methods known to those in the art, e.g.; L. F. Fieser and M. Fieser, supra.

The hydroxylamine may also be prepared by treatment of the epoxide with ammonia in a sealed vessel, see for example U.S. Pat. No. 4,332,804, which is incorporated herein by reference, particularly Preparation 3.

These compounds of formula A' can then be converted into the materials of formula E in Reaction Sequence 1 by reacting the resulting benzodioxan-2-yl hydroxyethyl amine derivatives with piperidone (formula B), by combining in a solvent such as methanol that will dissolve both reactants and a reducing agent, such as sodium cyanoborohydride, using methods described in the Examples.

The compounds of formula E may also be prepared by the treatment of compounds of formula A with 4-aminopiperidine in an inert solvent according to the method described in the Examples.

The compounds of formula F are prepared from the corresponding aniline, substituted aniline, or N-substituted aniline derivatives, of formula D which are commercially available, by reaction with α-haloacyl halides, such as monochloroacetyl chloride, or α-chloropropionyl chloride (compounds of formula C).

Many of the substituted anilines are commercially available. These include the methyl-, dimethyl-, trimethyl-, ethyl-, diethyl-, propyl-, butyl-, methoxy-, dimethoxy-, trimethoxy-, ethoxy-, diethoxy-, propoxy-, butoxy-, chloro-, dichloro-, trichloro-, tetrachloro-, pentachloro-, bromo-, dibromo-, tribromo-, fluoro-, difluoro-, trifluoro-, bromochloro-, bromofluoro-, chlorofluoro-, methylthio-, methylenedioxy-anilines and mixtures of the aforementioned compounds. Many N-alkylated aniline derivatives such as the N-methyl-, N-ethyl-, N-propyl- and N-butyl-anilines and substituted anilines are also commercially available according to *Chemical Sources*, published by Directories Publshing Company, Inc., Flemington, N.J. in 1979.

The methylsulfinyl and methylsulfonyl substituted anilines are prepared according to conventional procedures known in the art starting from the corresponding methylthioaniline, which is available from commercial sources. For instance, the o-methylsulfinylaniline is prepared by treating o-methylthioaniline with acetic anhydride to form the corresponding acetanilide which is then treated with sodium periodate in methanol. Upon hydrolysis to remove the acetyl group using acidic or basic conditions, there is obtained o-methylsulfinylaniline. The o-methylsulfonyl aniline is obtained by treating the acetanilide prepared above with hydrogen peroxide or 2-chloroperbenzoic acid in aqueous methanol. After hydrolysis to remove the acetyl group, there is obtained o-methylsulfonylaniline in good yield. The corresponding m- and p-substituted methylsulfinylanilines and methylsulfonylanilines are prepared by replacement of o-methylthioaniline by m-methyl and p-methylthioaniline respectively.

The corresponding ethyl-, propyl- and butyl-thioanilines are prepared by treatment of the commercially available aminothiophenol with sodium hydroxide followed by the appropriate alkyl iodide. The corresponding ethyl-, propyl- and butyl-sulfinyl and sulfonylanilines are prepared by replacement of o-methylthioaniline with the appropriate alkylthioaniline in the procedures described above.

Many N-alkyl substituted anilines may be prepared by procedures known in the art, such as treatment of the unsubstituted or aryl-substituted anilines described herein using an alkyl halide such as methyl chloride, ethyl chloride, propyl chloride, butyl chloride or the like in a suitable solvent such as diethylether or methylene dichloride.

Many α-halo acid halides are commercially available, including for example, chloroacetyl chloride and 2-chloropropionyl chloride. 2-Chlorobutyric acid is commercially available and may be converted to the acid chloride by methods known in the art, such as reaction with thionyl chloride or phosphorus pentachloride. The α- or 2-chloroacid chlorides which are not readily available may be prepared by conventional methods such as the Hell-Volhard-Zelinsky Reaction in which the appropriate alkyl carboxylic acid is reacted with chlorine in the presence of phosphorus. See for example, *Organic Chemistry*, by R. T. Morrison and R. N. Boyd, 2nd Edition, Ch. 18, p. 604 and *Chem. Revs.*, Vol 7, p. 180 (1930).

To carry out the reaction to produce compounds of formula F, the aniline derivative, a basic amine, such as triethylamine or pyridine, preferably triethylamine, and the chloroacyl chloride are dissolved in an inert aprotic organic solvent, such as, for example, benzene, chloroform, carbon tetrachloride, methylene or methylene chloride, preferably methylene chloride. The aniline and tertiary amine are in approximately equimolar amounts, and the acyl chloride is added in slight molar excess, about 1.2 or 2 L molar excess, preferably 1.3 to 1.5 molar excess compared to the aniline. The mixture is cooled to about $-10°$ C. to $+10°$ C., preferably in an ice bath, before the addition of the acyl halide. The mixture is maintained at this low temperature for approximately 2 to 8 hours, preferably about 4 hours with stirring. The resulting condensed product, of formula F, is then isolated by conventional means.

Compounds of formula I wherein Bzd and $R^1$ to $R^{11}$ are as defined above are prepared by reacting compounds of formula E with compounds of the formula F in a solvent such as toluene/methanol mixture, ethanol and dimethylformamide and the like. The reaction mixture is heated to a temperature of about 30° C. to about 150° C., preferably to about 70° C. to about 90° C. for about 6 hours to about 24 hours.

In some cases a mixture of products may be obtained because of the reaction of the halide with both the ring nitrogen and/or the amine attached at the 4-ring position. If these mixtures are present, they can be separated by techniques known in the art, such as fractional crystallization, chromatography and the like.

Isolation and purification of the compounds and intermediates described can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures could, of course, also be used.

The salt products are also isolated by conventional means. For example, the reaction mixtures may be evaporated to dryness, and the salts can be further purified by conventional methods.

The compounds of formula I produced by any of the Reaction Sequences described herein may exist as erythro and threo isomers. Accordingly, the compounds of the present invention may be prepared in either the erythro or threo forms (and the d- and l-forms) or as mixtures thereof. Unless specified, the compounds of the instant invention are a mixture of erythro and threo forms. However, the scope of the subject invention is not considered limited to the erythro/threo (or d-/l-) mixtures but encompasses the individual isomers of the subject compounds as well.

The pure erythro or threo isomers may be prepared by reacting the erythro or threo form of the intermediate epoxide (formula A) (See Gschwend references supra). If desired, a mixture of the intermediates used to prepare compounds of formula I or the final product may be separated by, e.g., recrystallization and chromatography. It is preferred to prepare the individual isomers from the isomeric intermediates of the compound of formula I.

Reaction Sequence 2

Alternatively, the compounds of formula I may be prepared according to Reaction Sequence 2 wherein Bzd, $R^1$ to $R^{11}$, Ar and X are as described above.

REACTION SEQUENCE 2

[Where m is 1, W is —N($R^6$)—, n is 1 and Q is Ar]

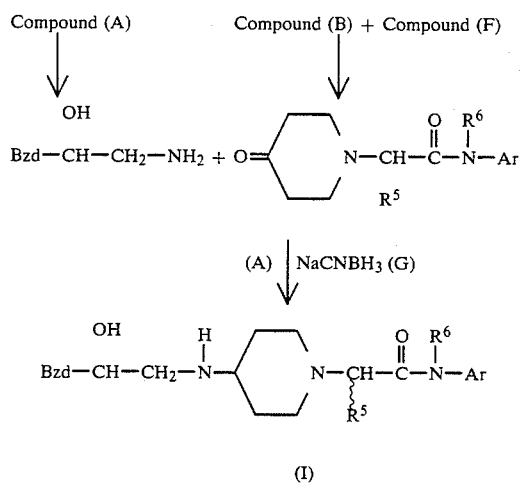

The compounds of formula F are produced by the reaction of a compound of formula C and a compound of formula D as was described above in Reaction Sequence 1.

The compounds of formula G are prepared from the corresponding compounds of formula F by reaction with piperidone (formula B), by means well known to those in the art, similar to those utilized above in converting the compounds of formula E and F into compounds of formula I. In this procedure, in both cases, the halide is mixed with an excess of piperidone, specifically a 1 to 2 molar excess, preferably about a 1 molar excess in a polar organic solvent, such as methanol, ethanol, propanol, or dimethylformamide, preferably methanol, in the presence of a molar equivalent of a reducing agent, such as sodium cyanoborohydride. The mixture is maintained at room temperature for about 12 to about 24 hr. The product of formula G may be isolated by conventional means.

The compounds of formula I are then prepared and isolated in a manner similar to that described above for the reaction of compounds of formulas A′ and B in Reaction Sequence 1 by combining the compounds of formulas A′ and G in the presence of sodium cyanoborohydride.

Reaction Sequence 2A

Alternatively, the compounds of formula I may be prepared according to Reaction Sequence 2A.

REACTION SEQUENCE 2A

[where m is 1, W is —N($R^6$)—, n is 1 and Q is Ar]

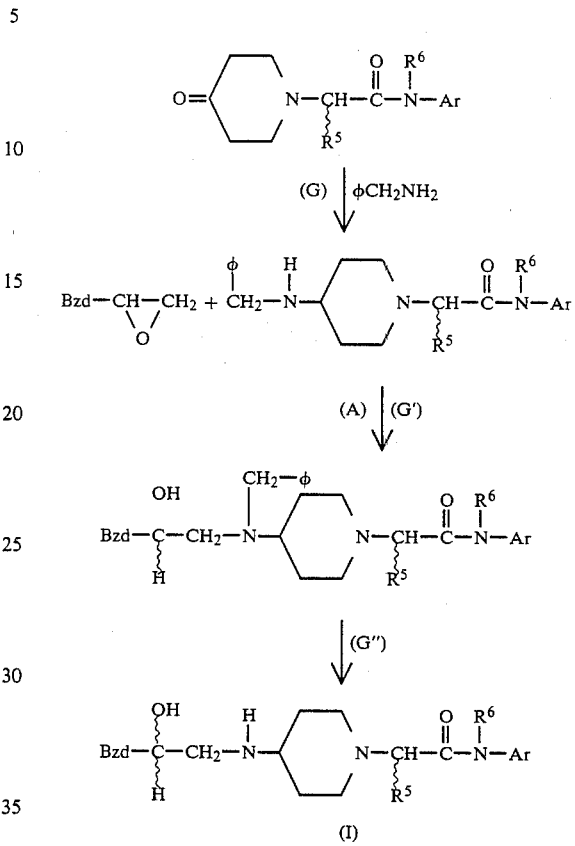

The compounds of formula A and G are prepared as is described in Reaction Sequences 1 and 2. Compound G is then treated with sodium cyanoborohydride, optionally in the presence of benzylamine, to produce the 4-(benzyl)amino piperidine which is subsequently coupled with the compound of formula A to produce the benzyl derivative (formula G″). The compound of formula G″ is then hydrogenated using, for instance, palladium-on-carbon catalyst to produce the compound of formula I.

Reaction Sequence 3

Alternatively, the compounds of formula I may be prepared according to Reaction Sequence 3.

REACTION SEQUENCE 3

[where m is 1, W is —N($R^6$)—, n is 1, and Q is Ar cycloalkyl or lower alkyl]

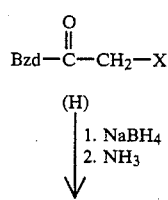

-continued

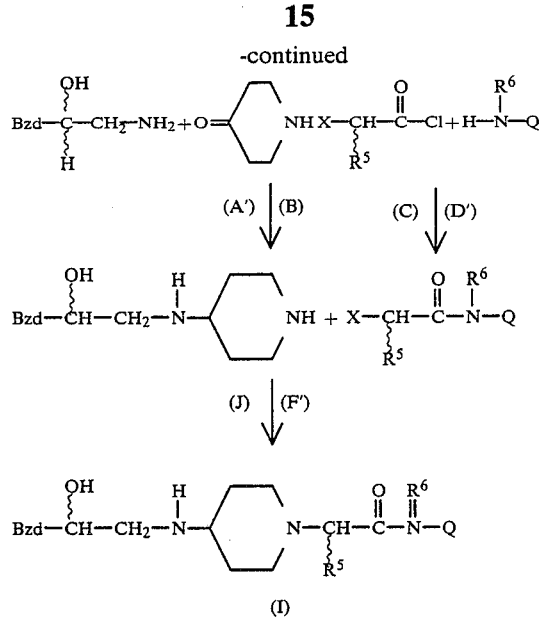

The (1,4-benzodioxan-2-yl)-α-bromomethyl ketones (formula H) are prepared by methods well known in the art, such as is described in *J. Med. Chem.*, vol. 13, 169 (1970) and *Organic Chemistry*, R. T. Morrison and R. N. Boyd, 2nd Ed., pp. 857–863, (1969).

The halide is reduced to the corresponding alcohol and when treated with ammonia under pressure in a sealed vessel at temperatures of 150°–250° C. produces the corresponding hydroxyethylamine (formula A').

Compounds of formula I wherein Q, Ar, Bzd, and $R^1$ to $R^{11}$ are as described above are prepared by reacting the appropriate compounds of formula F' with the appropriate (1,4-benzodioxan-2-yl)-2-hydroxyethyl amine; e.g., 2-(1,4-benzodioxan-2-yl)-2-hydroxyethyl]amine (formula A') [which is coupled with piperidone according to methods described in Reaction Sequences 1 and 2 above] to give a compound of formula J, ultimately to produce the compound of formula I.

Reaction Sequence 4

Alternatively the compounds of formula I may be prepared according to Reaction Sequence 4.

REACTION SEQUENCE 4

[where m is 0, W is —CH=CH—, n is 1 and Q is lower alkyl, cycloalkyl or Ar]

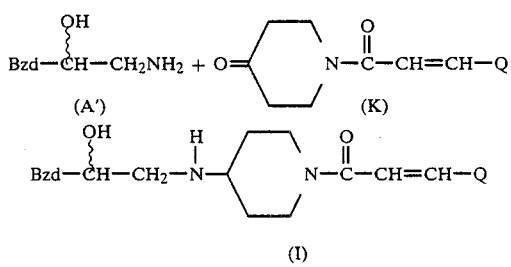

This method of preparing compounds of formula I wherein Ar, lower alkyl, Bzd, m, n, Q and W are as described herein uses the compound of formula A' as described in Reaction Sequence 1. When Q is phenyl, the optionally substituted cinnamoyl chloride is treated with piperidone, as the free base, at ambient temperature and pressure for 2 hours in a non hydroxylic solvent, such as methylene chloride. The compound of formula K is recovered after removal of the solvent and recrystallization from a solvent combination, such as ethyl acetate-hexane.

The compounds of formula A' and K are then combined in a hydroxylic solvent, such as methanol, in the presence of a reducing agent such as sodium cyanoborohydride and stirred for about 20 hours at ambient conditions. The product is dissolved in a solvent, such as methylene chloride, diluted with aqueous hydrogen chloride, treated with base and extracted with methylene chloride. The compound of formula I, as the hydrochloride salt, is recovered upon removal of the solvent.

Reaction Sequence 4A

Alternatively the compounds of formula I wherein m and n are each 0 and Q' is as described herein uses the compound of formula A' as described in Reaction Sequence 1. When Q is optionally substituted phenyl, cycloalkyl or lower alkyl, the corresponding commercially available or easily prepared optionally substituted aroyl, cycloalkyl carbonyl or acyl halides is treated with 4-piperidone and isolated and purified as is described in Reaction Sequence 4 or 5.

Alternatively, the compounds of formula I wherein m is 0 and n is 1 where W is alkylene and Q is described herein also starts with the compound of formula A' as described in Reaction Sequence 1. When W is alkylene and Q is optionally substituted phenyl, cycloalkyl, or lower alkyl, the corresponding commercially available or easily prepared optionally substituted aryl alkylene carbonyl, cycloalkylalkylenecarbonyl or acyl halide is treated with 4-piperidone and isolated and purified as is described in Reaction Sequences 4 or 5.

Reaction Sequence 5

Alternatively, the compounds of formula I may be prepared according to Reaction Sequence 5.

REACTION SEQUENCE 5

[Where m is 0, W is —N($R^6$)— or —O—, n is 1 and Q is lower alkyl, cycloalkyl or Ar]

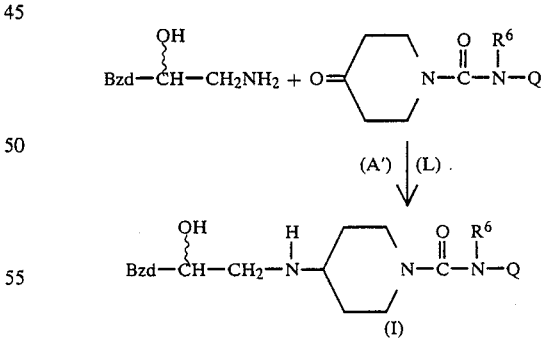

This method of preparing compounds of formula I wherein Ar, Bzd, m, n, Q and W are as described herein starts with the compound of formula A' as described in Reaction Sequence 1. When Q is phenyl, cyclohexyl or isopropyl, the commercially phenylisocyanate, cyclohexylisocyanate or isopropylisocyanate is treated with piperidone, as the free base at room temperature for two hours in a non-hydroxylic solvent, such as methylene or ethylene dichloride to produce the compound of formula L. When W is —N($R^6$)— the compound, X—C(=O)—N(R⁶)—Q, may also be used in this reaction, where X is halogen, such as chloro. The urea (or carbamate) compound of formula L is recovered after removal of the solvent and recrystallization from a solvent combination such as ethyl acetate-hexane.

When W is —O—, the compound, X—C(=O)—O—Q, may also be used in this reaction where X is halogen such, as chloro, and Q is as described herein. These compounds, where W is —O—, are commercially available or prepared by the reaction of the corresponding Q—OH with phosgene, $COCl_2$.

The compounds of formula A' and L are then combined in a hydroxylic solvent such as methanol in the presence of a reducing agent, such as sodium cyanoborohydride, and stirred for about 20 hours at ambient conditions. The product is dissolved in a solvent such as methylene chloride, diluted with aqueous hydrogen chloride, treated with base and extracted with methylene chloride. The compound of formula I, as the hydrochloride salt, is recovered upon removal of the solvent.

The compounds of formula I described herein may exist as mixtures of optical isomers because of the possible three asymmetric carbon atoms. Accordingly, the compounds of the present invention may be prepared in either optically active form (d- or l-) or as racemic mixtures (d, l-). Unless otherwise specified, the compounds described herein are all in the racemic form. However, the scope of the subject invention herein is not considered to be limited to a mixture of the racemic forms but to encompass all of the individual optical isomers as well.

If desired, racemic intermediates of compounds of formula A, A', C, D', E, F, F', G, G', J, K or L (supra) or final product, i.e., formula I prepared herein, may be resolved into their optical antipodes by conventional resolution means known in the art, for example, by the separation (e.g., fractional crystallization) of the diastereomeric salts formed by reaction of, e.g., racemic compounds of formula I or the intermediate compounds of formula A, A', C, D', E, F, F', G, G', J, K or L (supra) with an optically active acid. Exemplary of such optically active acids are the optically active forms of camphor-10-sulfonic acid, α-bromocamphor-π-sulfonic acid, camphoric acid, menthoxyacetic acid, tartaric acid, malic acid, diacetyltartaric acid, pyrrolidone-5-carboxylic acids, and the like and, where necessary, bases such as cinchonidine, brucine or the like. The separated pure diastereomeric salts may then be cleaved by standard means to afford the respective optical isomers of the compounds of formula I or the intermediates of formula A, A', C, D', E, F, F', G, G', J, K or L (supra).

The compounds of formula I may be isolated as free bases, but it is usually more convenient to isolate the compounds of the instant invention as acid addition salts. These salts are prepared in the usual manner, i.e., by reaction of the free base with a suitable organic or inorganic acid, for example, one of the pharmaceutically acceptable acids described above. The base of formula I, dissolved in an unreactive solvent such as an alcohol, e.g., methanol and ethanol, or an ether, e.g., diethyl ether and the like, is acidified with an acid dissolved in a like solvent. The acid solution is added until precipitation of the salt is complete. The reaction is carried out at a temperature of 20° to 50° C., preferably at room temperature. If desired, the salt can be readily converted to the free base by treatment with a base such as potassium or sodium carbonate or ammonium, potassium, or sodium hydroxide.

The compounds of formula I in free base form may be converted to the acid addition salts by treating with the appropriate organic or inorganic acid, such as, for example, phosphoric, pyruvic, hydrochloric or sulfuric acid and the like. Typically, the free base is dissolved in a polar organic solvent such as ethanol or methanol, and the acid added thereto. The temperature is maintained between about 0° C. and about 100° C. The resulting acid addition salt precipitates spontaneously or may be brought out of solution with a less polar solvent.

The acid addition salts of the compounds of formula I may be decomposed to the corresponding free base by treating with a suitable base, such as potassium carbonate or sodium hydroxide, typically in the presence of aqueous solvent, and at a temperature of between about 0° C. and about 100° C. The free base form is isolated by conventional means, such as extraction with an organic solvent.

Salts of the compounds of formula I may be interchanged by taking advantage of differential solubilities and volatilities, or by treating with the appropriately loaded ion exchange resin. This conversion is carried out at a temperature between about 0° C. and the boiling point of the solvent being used as the medium for the procedure.

In summary then, the compounds of formula I are prepared by:
reacting an unsubstituted or substituted 4-(benzodioxan-2-yl-2-hydroxyethylamino)piperidine (formula E) [which according to one alternative can be formed by the coupling of a benzodioxan-2-yl-2-hydroxyethylamine (formula A') with 4-piperidone (formula B) to form the 4-N-substituted piperidine (formula E)]; and
the substituted halo (alkyl) acetanilide (formula F) [which according to one alternative can be formed by the coupling of 2-haloalkylcarboxyl halide (formula C) with the unsubstituted or substituted aniline (formula D)].

Alternatively, the compounds of formula I are prepared by:
reacting an unsubstituted or substituted benzodioxan-2-yl-2-hydroxyethylamine (formula A'), and the ring N-substituted-4-piperidone (formula G) [which according to one alternative can be formed by the coupling of 2-haloalkylcarboxylhalide (formula C) with the unsubstituted or substituted aniline (formula D) to produce compound of formula F followed by coupling with 4-piperidone (formula B)].

Alternatively, the compounds of formula I are prepared by:
reacting the 4-N-substituted piperidine (formula J) [which according to one alternative can be formed by the coupling of an unsubstituted or substituted (benzodioxan-2-yl-2-hydroxyethyl)amine (formula A') with piperidone (formula B)] and the 2-halo (alkyl) acetanilide (formula F) [which according to one alternative can be formed by the coupling of 2-haloalkylcarboxyl halide (formula C) with unsubstituted or substituted aniline (formula D)] to produce the compound of formula I.

Alternatively, the compounds of formula I may also be prepared by:
the reaction of an unsubstituted or substituted benzodioxan-2-yl-2-hydroxyethylamine (formula A'), and coupling compound of formula L with an N-substituted carbonylethenylaryl piperidine (formula K) [which according to one alternative can be formed by the reaction of arylethenylcarboxyhalide (formula) with 4-piperidone (formula B)].

Alternatively, the compounds of formula I may also be prepared by:

reacting an unsubstituted or substituted benzodioxan-2-yl-2-hydroxyethylamine (formula A'), and the ring N-substituted-4-piperidone (Formula L) [which according to one alternative can be formed by the coupling of an aryl, cycloalkyl or lower alkyl isocyanate, acid halide or carbamate with 4-piperidone].

Alternatively, the compounds of formula I may also be prepared by:

reacting an unsubstituted or substituted (benzodioxan-2-yl-2-hydroxyethyl)amine (Formula A) and the ring N-substituted-4-piperidone [which according to one alternative can be formed by the coupling of an aryl, cycloalkyl or acyl halide with 4-piperidone].

Alternatively, the compound of formula I is prepared by converting a salt of formula I to a free base by using a stoichiometric excess of a base.

Alternatively, the free base of the compound of formula I is converted to a pharmaceutically acceptable acid addition salt by use of a stoichiometric excess of an acceptable acid.

Alternatively, the salt of the compound of formula I is converted to a different salt of the compound of formula I by use of a stoichiometric excess of an acceptable different acid.

UTILITY AND ADMINISTRATION

The compounds of the invention have been shown to effect $\beta$-blockade and calcium entry blockade in anesthesized dogs and in various in vitro animal preparations and tissue cultures, and accordingly are useful in the affecting physiological phenomena controlled by $\beta$-receptors. See for example, Kent et al., *Federation Proceedings*, Vol. 40, p. 724 (1981); Killam, et al., *Federation Proceedings*, Vol. 42, p. 1244 (1983); and Cotten et al., Journal Pharm. Exp. Therap., Vol. 121, pp. 183–190 (1957). Among these phenomena are blood pressure and heart rate, which is usually slowed. These compounds have been shown to be effective in animal models and are, therefore, useful in treating a cardiovascular disease, particularly myocardial infarction, arrhythmia, hypertension and variant and exercise-induced angina in a mammal, particularly a human being. The compounds of the invention have also been shown to be useful in the vasospastic disorders and as overload reducers in the treatment of congestive heart failure.

These compounds are also useful as immunosuppressants, and in particular they are useful in the treatment of autoimmune diseases such as rheumatoid arthritis.

Administration of the active compounds and salts described herein can be via any of the accepted modes of administration for therapeutic agents which affect $\beta$-receptors. These methods include oral, parenteral, transdermal, subcutaneous and other systemic modes. The preferred method of administration is oral, except in those cases where the subject is unable to ingest, by himself, any medication. In those instances it may be necessary to administer the composition parenterally.

Depending on the intended mode, the compositions may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical excipient and an active compound of formula I or the pharmaceutically acceptable salts thereof and, in addition, may include other medicinal agents, pharmaceutical agents, carriers, adjuvants, diluents, etc.

The amount of active compound administered will, of course, be dependent on the subject being treated, the severity of the affliction, the manner of administration and the judgment of the prescribing physician. However, an effective dosage is in the range of 0.1–10 mg/kg/day, preferably 0.5–5 mg/kg/day. For an average 70 kg human, this would amount to 7–700 mg per day, or preferably 35–350 mg/day.

Since the effects of the compounds herein (antiarrhythmia, antimyocardial infarction, antihypertension, and variant and exercise induced angina inhibition) are achieved through the same central mechanism (effecting $\beta$-blockade and calcium entry blockade in the adrenergic system) dosages (and forms of administration) are within the same general and preferred ranges for all these utilities.

For solid compositions, conventional non-toxic solid include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s), a thereuptically effective amount, i.e. in an amount effective to alleviate the symptoms of the subject being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 1–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795, which is incorporated herein by reference.

The following preparations and examples serve to illustrate the invention. They should not be construed as narrowing it, or limiting its scope.

PREPARATION A (Preparation of Compounds of Formula A)

(a) To a solution of 1.32 g of catechol (1,2-benzenediol) in 15 ml of dimethylsulfoxide, 0.8 g of sodium hydroxide pellets is added while stirring under nitrogen at 55° C. After about 4 hours the dark green solution is combined with 1.5 g of trans-2,3-bis-chloromethyloxirane and stirring is continued for 4 hours at 55°–60° C. After cooling to room temperature the mixture is diluted with 100 ml of water and extracted with diethyl ether. The extract is washed with aqueous sodium hydroxide and saturated aqueous sodium chloride, dried and evaporated to yield 1.6 g of a light yellow oil. It is chromatographed on silica gel using chloroform to yield, after evaporation, 0.9 g of a colorless oil which solidifies on standing. It is crystallized from diethyl ether to yield the d,l-erythro-2-(1,4-benzodioxan-2-yl)-2-epoxide, mp 51°–52° C.

(b) Similarly, proceeding as in Subpart (a) above, but substituting a stoichiometrically equivalent amount of:
4-methyl-1,2-benzenediol;
4-n-butyl-1,2-benzendiol;
4-methoxy-1,2-benzenediol;
4-n-butoxy-1,2-benzenediol;
4-chloro-1,2-benzenediol;
4-bromo-1,2-benzenediol;
5-methyl-1,2-benzenediol;
5-methoxy-1,2-benzenediol;
5-chloro-1,2-benzenediol;
4,5-dimethyl-1,2-benzenediol;
4,5-dichloro-1,2-benzenediol;
4-methyl-5-chloro-1,2-benzenediol;
3,4,5-trichloro-1,2-benzenediol;
3-methyl-4,5-dichloro-1,2-benzenediol;
3-methyl-4-chloro-5-methoxy-1,2-benzenediol;
3,4,5,6-tetrabromo-1,2-benzenediol;
3,6-dimethyl-4,5-dichloro-1,2-benzenediol;
4-trifluoromethyl-1,2-benzenediol;
4-methylthio-1,2-benzenediol;
4-n-butylthio-1,2-benzenediol;
4-methylsulfinyl-1,2-benzenediol;
4-n-butylsulfinyl-1,2-benzenediol;
4-methylsulfonyl-1,2-benzenediol; or
4-n-butylsulfonyl-1,2-benzenediol
for catechol, the following d,l-erythro epoxide compounds of formula A are obtained:
2-(6-methyl-1,4-benzodioxan-2-yl)-2-epoxide;
2-(6-n-butyl-1,4-benzodioxan-2-yl)-2-epoxide;
2-(6-methoxy-1,4-benzodioxan-2-yl)-2-epoxide;
2-(6-n-butoxy-1,4-benzodioxan-2-yl)-2epoxide;
2-(6-chloro-1,4-benzodioxan-2-yl)-2-epoxide;
2-(6-bromo-1,4-benzodioxan-2-yl)-2-epoxide;
2-(7-methyl-1,4-benzodioxan-2-yl)-2-epoxide;
2-(7-methoxy-1,4-benzodioxan-2-yl)-2-epoxide;
2-(7-chloro-1,4-benzodioxan-2-yl)-2-epoxide;
2-(6,7-dimethyl-1,4-benzodioxan-2-yl)-2-epoxide;
2-(6,7-dichloro-1,4-benzodioxan-2-yl)-2-epoxide;
2-(6-methyl-7-chloro-1,4-benzodioxan-2-yl)-2-epoxide;
2-(5,6,7-trichloro-1,4-benzodioxan-2-yl)-2-epoxide;
2-(5-methyl-6,7-dichloro-1,4-benzodioxan-2-yl)-2-epoxide;
2-(5-methyl-6-chloro-7-methoxy-1,4-benzodioxan-2-yl)-2-epoxide;
2-(5,6,7,8-tetrabromo-1,4-benzodioxan-2-yl)-2-epoxide;
2-(5,8-dimethyl-6,7-dichloro-1,2-benzodioxan-2-yl)-2-epoxide;
2-(6-trifluoromethyl-1,2-benzodioxan-2-yl)-2-epoxide;
2-(6-methylthio-1,2-benzodioxan-2-yl)-2-epoxide;
2-(6-n-butylthio-1,2-benzodioxan-2-yl)-2-epoxide;
2-(6-methylsulfinyl-1,2-benzodioxan-2-yl)-2-epoxide;
2-(6-n-butylsulfinyl-1,2-benzodioxan-2-yl)-2-epoxide;
2-(6-methylsulfonyl-1,2-benzodioxan-2-yl)-2-epoxide;
or
2-(6-n-butylsulfonyl-1,2-benzodioxan-2-yl)-2-epoxide.
These compounds are of sufficient purity for use in Reaction Sequences 1 to 5.

(c) Similarly, proceeding as in Subpart (a) of this Preparation but substituting a stoichiometrically equivalent amount of cis-2,3-bischloromethyloxirane for trans-2,3-bischloromethyloxirane, there is obtained the d,l-threo-2-(1,4-benzodioxan-2-yl)-2-epoxide in good yield.

(d) Similarly, proceeding as in Subpart (c) of this Preparation but substituting a stoichiometrically equivalent amount of the optionally substituted benzenediols cited in Subpart (b) for catechol, the corresponding d,l-threo epoxide components of formula A are obtained.

(e) Similarly, proceeding in Subpart (a) of this Preparation but substituting a stoichiometrically equivalent amount of a mixture of cis-2,3-bis-chloromethyloxirane and trans-2,3-bis-chloromethyloxirane for trans-2,3-bis-chloromethyloxirane, there is obtained a corresponding mixture of d,l-erythro-2-(1,4-benzodioxan-2-yl)-2-epoxide and d,l-threo-2-(1,4-benzodioxan-2-yl)-2-epoxide in good yield.

(f) Similarly, proceeding in Subpart (a) of this Preparation but substituting a stoichiometrically equivalent amount of a mixture of cis- and trans-2,3-bis-chloromethyloxirane for trans-2,3-bischloromethyloxirane and an aryl substituted catechol (substituted 1,2-benzenediol) for catechol, there is obtained a corresponding mixture of d,l-erythro- and d,l-threo-2-(optionally substituted 1,4-benzodioxan-2-yl)-2-epoxide in good yield.

PREPARATION A'

(Preparation of Compound of Formula A')

(a) To a solution of dioxane (125 ml) and water (38 ml) is added d,l-erythro-2-(1,4-benzodioxany-2-yl)-2-epoxide (18.8 g) and sodium azide (13 g). The solution is heated at about 100° C. for 6 hr and then overnight (about 16 hr) at about 80° C. Thin layer chromatographic analysis (50% ether/hexane) indicates that the reaction is complete. The product is added to water extracted twice with diethylether, washed twice with water, twice with brine, dried and evaporated to an oil, yield 20 g.

Without further purification the azide, as an oil in 100 ml of tetrahydrofuran, is slowly added dropwise to 100 ml of tetrahydrofuran containing 3 g of lithium aluminum hydride. The reaction is stirred for one hour at ambient conditions. Thin layer chromatographic analysis indicates the reaction is complete. To the solution is slowly added 3 ml of water, 3 ml of 15% sodium hydroxide solution and 9 ml of water. The solution is filtered and the solvent evaporated. The product, [2-(1,4-benzodioxan-2-yl)-2-hydroxyethyl]amine as the hydrochloride salt has a mp 197°-198° C.

(b) Similarily proceeding as in Subpart (a) of this Preparation but substituting a stoichiometrically equivalent amount of:

2-(6-methyl-1,4-benzodioxan-2-yl)-2-epoxide;
2-(6-n-butyl-1,4-benzodioxan-2-yl)-2-epoxide;
2-(6-methoxy-1,4-benzodioxan-2-yl)-2-epoxide;
2-(6-n-butoxy-1,4-benzodioxan-2-yl)-2-epoxide;
2-(6-chloro-1,4-benzodioxan-2-yl)-2-epoxide;
2-(6-bromo-1,4-benzodioxan-2-yl)-2-epoxide;
2-(7-methyl-1,4-benzodioxan-2-yl)-2-epoxide;
2-(7-methoxy-1,4-benzodioxan-2-yl)-2-epoxide;
2-(7-chloro-1,4-benzodioxan-2-yl)-2-epoxide;
2-(6,7-dimethyl-1,4-benzodioxan-2-yl)-2-epoxide;
2-(6,7-dichloro-1,4-benzodioxan-2-yl)-2-epoxide;
2-(6-methyl-7-chloro-1,4-benzodioxan-2-yl)-2-epoxide;
2-(5,6,7-trichloro-1,4-benzodioxan-2-yl)-2-epoxide;
2-(5-methyl-6,7-dichloro-1,4-benzodioxan-2-yl)-2-epoxide;
2-(5-methyl-6-chloro-7-methoxy-1,4-benzodioxan-2-yl)-2-epoxide;
2-(5,6,7,8-tetrabromo-1,4-benzodioxan-2-yl)-2-epoxide;
2-(5,8-dimethyl-6,7-dichloro-1,2-benzodioxan-2-yl)-2-epoxide;
2-(6-trifluoromethyl-1,4-benzodioxan-2-yl)-2-epoxide;
2-(6-methylthio-1,4-benzodioxan-2-yl)-2-epoxide;
2-(6-n-butylthio-1,4-benzodioxan-2-yl)-2-epoxide;
2-(6-methylsulfinyl-1,4-benzodioxan-2-yl)-2-epoxide;
2-(6-n-butylsulfinyl-1,4-benzodioxan-2-yl)-2-epoxide;
2-(6-methylsulfonyl-1,4-benzodioxan-2-yl)-2-epoxide; or
2-(6-n-butylsulfonyl-1,4-benzodioxan-2-yl)-2-epoxide for 2-(1,4-benzodioxan-2-yl)-2-epoxide, the following d,l-erythro amine compounds of formula A' are obtained:

[2-(6-methyl-1,4-benzodioxan-2-yl)-2-hydroxyethyl]amine;
[2-(6-n-butyl-1,4-benzodioxan-2-yl)-2-hydroxyethyl]amine;
[2-(6-methoxy-1,4-benzodioxan-2-yl)-2-hydroxyethyl]amine;
[2-(6-n-butoxy-1,4-benzodioxan-2-yl)-2-hydroxyethyl]amine;
[2-(6-chloro-1,4-benzodioxan-2-yl)-2-hydroxyethyl]amine;
[2-(6-bromo-1,4-benzodioxan-2-yl)-2-hydroxyethyl]amine;
[2-(7-methyl-1,4-benzodioxan-2-yl)-2-hydroxyethyl]amine;
[2-(7-methoxy-1,4-benzodioxan-2-yl)-2-hydroxyethyl]amine;
[2-(7-chloro-1,4-benzodioxan-2-yl)-2-hydroxyethyl]amine;
[2-(6,7-dimethyl-1,4-benzodioxan-2-yl)-2-hydroxyethyl]amine;
[2-(6,7-dichloro-1,4-benzodioxan-2-yl)-2-hydroxyethyl]amine;
[2-(6-methyl-7-chloro-1,4-benzodioxan-2-yl)-2-hydroxyethyl]amine;
[2-(5,6,7-trichloro-1,4-benzodioxan-2-yl)-2-hydroxyethyl]amine;
[2-(5-methyl-6,7-dichloro-1,4-benzodioxan-2-yl)-2-hydroxyethyl]amine;
[2-(5-methyl-6-chloro-7-methoxy-1,4-benzodioxan-2-yl)-2-hydroxyethyl]amine;
[2-(5,6,7,8-tetrabromo-1,4-benzodioxan-2-yl)-2-hydroxyethyl]amine;
[2-(5,8-dimethyl-6,7-dichloro-1,4-benzodioxan-2-yl)-2-hydroxyethyl]amine;
[2-(6-trifluoromethyl-1,4-benzodioxan-2-yl)-2-hydroxyethyl]amine;
[2-(6-methylthio-1,4-benzodioxan-2-yl)-2-hydroxyethyl]amine;
[2-(6-n-butylthio-1,4-benzodioxan-2-yl)-2-hydroxyethyl]amine;
[2-(6-methylsulfinyl-1,4-benzodioxan-2-yl)-2-hydroxyethyl]amine;
[2-(6-n-butylsulfinyl-1,4-benzodioxan-2-yl)-2-hydroxyethyl]amine;
[2-(6-methylsulfonyl-1,4-benzodioxan-2-yl)-2-hydroxyethyl]amine; or
[2-(6-n-butylsulfonyl-1,4-benzodioxan-2-yl)-2-hydroxyethyl]amine. These compounds are of sufficient purity for use in this invention.

(c) Similarly, proceeding as in Subpart (a) of this Preparation but substituting a stoichiometrically equivalent amount of d,l-threo-2-(1,4-benzodioxan-2-yl)-2-epoxide for d,l-erythro-2-(1,4-benzodioxan-2-yl)-2-epoxide, there is obtained the d,l-threo-[2-(1,4-benzodioxan-2-yl)-2-hydroxyethyl]amine in good yield.

(d) Similarly, proceeding as in Subpart (c) of this Preparation but substituting a stoichiometrically equivalent amount of the substituted d,l-threo-2-(1,4-benzodioxan-2-yl)-2-epoxides cited for 2-(1,4-benzodioxan-2-yl)-2-epoxide, the corresponding d,l-threo-2-(1,4-benzodioxan-2-yl)-2-hydroxyethylamine compounds of formula A' are obtained.

(e) Similarly, proceeding in Subpart (a) of this Preparation but substituting a stoichiometrically equivalent amount of a mixture of d,l-erythro-2-(1,4-benzodioxan-2-yl)-2-epoxide and d,l-threo-2-(1,4-benzodioxan-2-yl)-2-epoxide for 1,4-benzodioxan-2-yl-2-epoxide, there is obtained a corresponding mixture of d,l-erythro-[1-(1,4-benzodioxan-2-yl)-2-hydroxyethyl]amine and d,l-threo-[2-(1,4-benzodioxan-2-yl)-2-hydroxyethyl]amine in good yield.

(f) Similarly, proceeding in Subpart (b) of this Preparation but substituting a stoichiometrically equivalent amount of a mixture of d,l-erythro and d,l-threo aryl substituted-2-(1,4-benzodioxan-2-yl)-2-epoxide for d,l-threo-1,4-benzodioxan-2-yl-2-epoxide, there is obtained a corresponding mixture of d,l-erythro- and d,l-threo-[2-(aryl substituted-1,4-benzodioxan-2-yl)-2-hydroxyethyl]amine in good yield.

PREPARATION A"

(Preparation of Compounds of formula E)

(a) The [2-(1,4-benzodioxan-2-yl)-2-hydroxyethyl]amine prepared in Preparation A' (50 g) and piperidone (85 g) are dissolved in 500 ml of ethanol. Seventy-five grams of sodium cyanoborohydride is added, and the mixture is maintained at room temperature for 12 hours and cooled and evaporated. The product is recovered by adding aqueous ammonia to the residue and extracting with methylene chloride. Three 100 ml portions of methylene chloride are used which are combined, washed twice with 50 ml of water and evaporated to a semi-solid. Upon addition of ether, the product crystallizes and is recovered by filtration. The resulting crude mixture is boiled gently in 100 ml of diethyl ether and then evaporated to a residue and triturated with hexane to yield pure material, 4-{[2-(1,4-benzodioxan-2-yl)-2-hydroxyethyl]amino}piperidine.

(b) In a corresponding manner to that described in Preparation A, Subparts (b) to (f), when a stoichiometrically equivalent amount of optionally substituted d,l-erythro- or d,l-threo-[2-(1,4-benzodioxan-2-yl)-2-hydroxyethyl]amine or mixtures thereof is substituted for [2-(1,4-benzodioxan-2-yl)-2-hydroxyethyl]amine, there is obtained the corresponding d,l-erythro-, d,l-threo-4-{[2-(1,4-benzodioxan-2-yl)-2-hydroxyethyl]amino}piperidine or mixtures thereof, respectively.

PREPARATION B

Preparation of [(2,6-dimethylphenyl)aminocarbonylmethyl]chloride (Compound of formula F, where Q is Ar)

(a) 2,6-Dimethylaniline (96 g, 793 mmoles) and triethylamine (TEA) (96 g, 130 ml) are dissolved in one liter of methylene chloride. The mixture is cooled in ice, and the chloroacetyl chloride (89.6 g, 800 mmoles) is added slowly. The mixture is stirred for 4 hours and becomes very dark in color. The mixture is then washed with dilute hydrochloric acid, and concentrated under vacuum. Hexane is added to precipitate the product, [(2,6-dimethylphenyl)aminocarbonylmethyl]chloride, and the crude product is filtered, is washed and dried. A yield of 130 g is obtained, in sufficient purity for use in Reaction Sequences 1 to 5.

(b) Repeating the above procedure in a similar manner and substituting a stoichiometrically equivalent amount of:
aniline;
2-chloroaniline;
3-chloroaniline;
4-chloroaniline;
2-bromoaniline;
3-bromoaniline;
4-bromoaniline;
2-fluoroaniline;
3-fluoroaniline;
4-fluoroaniline;
2-methylaniline;
3-methylaniline;
4-methylaniline;
4-n-butylaniline;
2-methoxyaniline;
3-methoxyaniline;
4-methoxyaniline;
4-n-butoxyaniline;
4-hydroxyaniline;
4-aminosulfonylaniline;
2-trifluoromethylaniline;
3-trifluoromethylaniline;
4-trifluoromethylaniline;
2,6-dichloroaniline;
3,5-dimethoxyaniline;
3,4-methylenedioxyaniline;
2-chloro-5-methylaniline;
4-methylthioaniline;
4-methylsulfinylaniline;
4-methylsulfonylaniline;
4-n-butylthioaniline;
4-n-butylsulfinylaniline;
4-n-butylsulfonylaniline;
3,4-difluoroaniline;
2,5-diethoxyaniline;
2,4,5-trichloroaniline;
3,4,5-trimethoxyaniline;
2,4,5,6-tetrachloroaniline;
2,3,4,6-tetramethylaniline;
2,3,4,5,6-pentachloroaniline;
3-chloro-2,4,6-trimethylaniline;
N-methylaniline;
N-n-butylaniline;
N-methyl-2,6-dimethylaniline;
N-n-butyl-2,6-dimethylaniline;
methylamine;
isopropylamine;
n-butylamine;
cyclopropylamine;
cyclohexylamine; or
cyclooctylamine for 2,6-dimethylaniline, there are obtained the following substituted chlorides of formula F:
(phenylaminocarbonylmethyl)chloride;
[(2-chlorophenyl)aminocarbonylmethyl]chloride;
[(3-chlorophenyl)aminocarbonylmethyl]chloride;
[(4-chlorophenyl)aminocarbonylmethyl]chloride;
[(2-bromophenyl)aminocarbonylmethyl]chloride;
[(3-bromophenyl)aminocarbonylmethyl]chloride;
[(4-bromophenyl)aminocarbonylmethyl]chloride;
[(2-fluorophenyl)aminocarbonylmethyl]chloride;
[(3-fluorophenyl)aminocarbonylmethyl]chloride;
[(4-fluorophenyl)aminocarbonylmethyl]chloride;
[(2-methylphenyl)aminocarbonylmethyl]chloride;
[(3-methylphenyl)aminocarbonylmethyl]chloride;
[(4-methylphenyl)aminocarbonylmethyl]chloride;
[(4-n-butylphenyl)aminocarbonylmethyl]chloride;
[(2-methoxyphenyl)aminocarbonylmethyl]chloride;
[(3-methoxyphenyl)aminocarbonylmethyl]chloride;
[(4-methoxyphenyl)aminocarbonylmethyl]chloride;
[(4-n-butoxyphenyl)aminocarbonylmethyl]chloride;
[(4-hydroxyphenyl)aminocarbonylmethyl]chloride;
[(4-aminosulfonylphenyl)aminocarbonylmethyl]chloride;
[(2-trifluoromethylphenyl)aminocarbonylmethyl]chloride;
[(3-trifluoromethylphenyl)aminocarbonylmethyl]chloride;
[(4-trifluoromethylphenyl)aminocarbonylmethyl]chloride;
[(2,6-dichlorophenyl)aminocarbonylmethyl]chloride;
[(3,5-dimethoxyphenyl)aminocarbonylmethyl]chloride;
[(3,4-methylenedioxyphenyl)aminocarbonylmethyl]chloride;
[(2-chloro-5-methylphenyl)aminocarbonylmethyl]chloride;
[(4-methylthiophenyl)aminocarbonylmethyl]chloride;
[(4-methylsulfinylphenyl)aminocarbonylmethyl]chloride;
[(4-methylsulfonylphenyl)aminocarbonylmethyl]chloride;
[(4-n-butylthiophenyl)aminocarbonylmethyl]chloride;
[(4-n-butylsulfinylphenyl)aminocarbonylmethyl]chloride;
[(4-n-butylsulfonylphenyl)aminocarbonylmethyl]chloride;
[(3,4-difluorophenyl)aminocarbonylmethyl]chloride;
[(2,5-diethoxyphenyl)aminocarbonylmethyl]chloride;
[(2,4,5-trichlorophenyl)aminocarbonylmethyl]chloride;

[(3,4,5-trimethoxyphenyl)aminocarbonylmethyl]chloride;
[(2,4,5,6-tetrachlorophenyl)aminocarbonylmethyl]chloride;
[(2,3,4,6-tetramethylphenyl)aminocarbonylmethyl]chloride;
[(2,3,4,5,6-pentachlorophenyl)aminocarbonylmethyl]chloride;
[(3-chloro-2,4,6-trimethylphenyl)aminocarbonylmethyl]chloride;
[N-methyl-N-(phenyl)aminocarbonylmethyl]chloride;
[N-n-butyl-N-(phenyl)aminocarbonylmethyl]chloride;
[N-methyl-N-(2,6-dimethylphenyl)aminocarbonylmethyl]chloride;
[N-n-butyl-N-(2,6-dimethylphenyl)aminocarbonylmethyl]chloride;
[N-(methyl)aminocarbonylmethyl]chloride;
[N-(isopropyl)aminocarbonylmethyl]chloride;
[N-(n-butyl)aminocarbonylmethyl]chloride;
[N-(cyclopropyl)aminocarbonylmethyl]chloride;
[N-(cyclohexyl)aminocarbonylmethyl]chloride; or
[N-(cyclooctyl)aminocarbonylmethyl]chloride
of sufficient purity for use in this invention.

(c) Repeating the above procedure in Subpart (a) in a similar manner and substituting a stoichiometrically equivalent amount of:
2-chloropropanoyl chloride;
2-chloro-n-butanoyl chloride; or
2-chloro-n-hexanoyl chloride;
for chloroacetylchloride, there are obtained the following substituted chlorides of formula F:
[(2,6-dimethylphenyl)aminocarbonyl-1-ethyl]chloride;
[(2,6-dimethylphenyl)aminocarbonyl)-1-n-propyl]chloride; or
[(2,6-dimethylphenyl)aminocarbonyl-1-n-pentyl]chloride.

(d) Repeating the above procedure in a similar manner and substituting a stoichiometrically equivalent amount of;
aniline;
N-methyl-2,6-dimethylaniline; or
N-n-butyl-2,6-dimethylaniline
for 2,6-dimethylaniline and 2-chloropropanoyl chloride for chloroacetyl chloride, this is obtained the corresponding
[phenylaminocarbonyl-1-ethyl]chloride;
[N-methyl-N-(2,6-dimethylphenyl)aminocarbonyl-1-ethyl]chloride; or
[N-n-butyl-N-(2,6-dimethylphenyl)aminocarbonyl-1-ethyl]chloride.

(e) Repeating the above procedure in Subpart (a) in a similar manner and substituting a stoichiometrically equivalent amount of
aniline;
N-methyl-2,6-dimethylaniline; or
N-n-butyl-2,6-dimethylaniline
for 2,6-dimethylaniline, and 2-chloro-n-hexanoyl chloride for chloroacetyl chloride there is obtained the corresponding
[(phenyl)aminocarbonyl-1-n-pentyl]chloride;
[N-methyl-N-(2,6-dimethylphenyl)aminocarbonyl-1-n-pentyl]chloride; or
[N-n-butyl-N-(2,6-dimethylphenyl)aminocarbonyl-1-n-pentyl]chloride.

PREPARATION C

Preparation of 1-[(2,6-dimethylphenyl)aminocarbonylmethyl]-4-piperidone (Compound of formula G)

(a) The crude [(2,6-dimethylphenyl)aminocarbonylmethyl]chloride, prepared in Preparation B (50 g., 0.25 moles) and 4-piperidone (86 g, 1 mole) are dissolved in 500 ml of ethanol. The mixture is refluxed for two hours, and then cooled and evaporated. The product is recovered by adding aqueous ammonia to the residue, and extracting with methylene chloride. Three portions of methylene chloride are used, which are collected, washed with water, and evaporated to a semi-solid. Upon addition of diethylether, the product crystallizes and is filtered. The resulting crude mixture is boiled with ether and then evaporated to a residue and triturated with hexane to yield pure material, 1-[(2,6-dimethylphenyl)aminocarbonylmethyl]-4-piperidone. This material is of sufficient purity for use in Reaction Sequences 2 to 5.

(b) Repeating the above procedure [Subpart (a)] in a similar manner and substituting a stoichiometrically equivalent amount of:
phenylaminocarbonylmethylchloride;
[(4-chlorophenyl)aminocarbonylmethyl]chloride;
[(4-fluorophenyl)aminocarbonylmethyl]chloride;
[(4-methylphenyl)aminocarbonylmethyl]chloride;
[(4-methoxyphenyl)aminocarbonylmethyl]chloride;
[(3-chlorophenyl)aminocarbonylmethyl]chloride;
[(4-hydroxyphenyl)aminocarbonylmethyl]chloride;
[(4-aminosulfonylphenyl)aminocarbonylmethyl]chloride;
[(3,4-methylenedioxyphenyl)aminocarbonylmethyl]chloride;
[(2,6-dichlorophenyl)aminocarbonylmethyl]chloride;
[(2,4,6-trimethylphenyl)aminocarbonylmethyl]chloride;
[(3,5-dimethoxyphenyl)aminocarbonylmethyl]chloride;
[(4-methylthiophenyl)aminocarbonylmethyl]chloride;
[(4-n-butylthiophenyl)aminocarbonylmethyl]chloride;
[(4-methylsulfinylphenyl)aminocarbonylmethyl]chloride;
[(4-n-butylsulfinylphenyl)aminocarbonylmethyl]chloride;
[(4-methylsulfonylphenyl)aminocarbonylmethyl]chloride;
[(4-n-butylsulfonylphenyl)aminocarbonylmethyl]chloride;
[(3-trifluoromethylphenyl)aminocarbonylmethyl]chloride;
[(4-trifluoromethylphenyl)aminocarbonylmethyl]chloride;
[(2-chloro-5-methylphenyl)aminocarbonylmethyl]chloride;
[(3,5-difluorophenyl)aminocarbonylmethyl]chloride;
[(2,6-diethoxyphenyl)aminocarbonylmethyl]chloride;
[(3-bromo-4-ethylphenyl)aminocarbonylmethyl]chloride;
[(4-n-butylphenyl)aminocarbonylmethyl]chloride;
[(4-isobutylphenyl)aminocarbonylmethyl]chloride;
[(3,4,5-trimethoxyphenyl)aminocarbonylmethyl]chloride;
[(2,3,4,5-tetrachlorophenyl)aminocarbonylmethyl]chloride;

[(2,3,4,5,6-pentachlorophenyl)aminocarbonylmethyl]-chloride;
[N-methyl-N-(phenyl)aminocarbonylmethyl]chloride;
[N-n-butyl-N-(phenyl)aminocarbonylmethyl]chloride;
[N-methyl-N-(2,6-dimethylphenyl)aminocarbonylmethyl]chloride;
[N-n-butyl-N-(2,6-dimethylphenyl)aminocarbonylmethyl]chloride;
[(2,6-dimethylphenyl)aminocarbonyl-1-ethyl]chloride;
[N-methyl-N-(2,6-dimethylphenyl)aminocarbonyl-1-ethyl]chloride;
[N-n-butyl-N-(2,6-dimethylphenyl)aminocarbonyl-1-ethyl]chloride;
[(2,6-dimethylphenyl)aminocarbonyl-1-n-pentyl]chloride;
[N-methyl-N-(2,6-dimethylphenyl)aminocarbonyl-1-n-pentyl]chloride;
[N-n-butyl-N-(2,6-dimethylphenyl)aminocarbonyl-1-n-pentyl]chloride;
[N-(methyl)aminocarbonylmethyl]chloride;
[N-(isopropyl)aminocarbonylmethyl]chloride;
[N-(n-butyl)aminocarbonylmethyl]chloride;
[N-(cyclopropyl)aminocarbonylmethyl]chloride;
[N-(cyclohexyl)aminocarbonylmethyl]chloride; or
[N-(cyclooctyl)aminocarbonylmethyl]chloride
1-[(4-trifluoromethylphenyl)aminocarbonylmethyl]-4-piperidone;
1-[(2-chloro-5-methylphenyl)aminocarbonylmethyl]-4-piperidone;
1-[(3,5-difluorophenyl)aminocarbonylmethyl]-4-piperidone;
1-[(2,6-diethoxyphenyl)aminocarbonylmethyl]-4-piperidone;
1-[(3-bromo-4-ethylphenyl)aminocarbonylmethyl]-4-piperidone;
1-[(4-n-butylphenyl)aminocarbonylmethyl]-4-piperidone;
1-[(4-isobutylphenyl)aminocarbonylmethyl]-4-piperidone;
1-[(3,4,5-trimethoxyphenyl)aminocarbonylmethyl]-4-piperidone;
1-[(2,3,4,5-tetrachlorophenyl)aminocarbonylmethyl]-4-piperidone;
1-[(2,3,4,5,6-pentachlorophenyl)aminocarbonylmethyl]-4-piperidone;
1-[N-methyl-N-(phenyl)aminocarbonylmethyl]-4-piperidone;
1-[N-n-butyl-N-(phenyl)aminocarbonylmethyl]-4-piperidone;
1-[N-methyl-N-(2,6-dimethylphenyl)aminocarbonylmethyl]-4-piperidone;
1-[N-n-butyl-N-(2,6-dimethylphenyl)aminocarbonylmethyl]-4-piperidone;
1-[(2,6-dimethylphenyl)aminocarbonyl-1-ethyl]-4-piperidone;
1-[N-methyl-N-(2,6-dimethylphenyl)aminocarbonyl-1-ethyl]-4-piperidone;
1-[N-n-butyl-N-2,6-dimethylphenyl)aminocarbonyl-1-ethyl]-4-piperidone;
for [(2,6-dimethylphenyl)aminocarbonylmethyl]chloride, there are obtained the following 4-piperidones:
1-(phenylaminocarbonylmethyl)-4-piperidone;
1-[4-chlorophenyl)aminocarbonylmethyl]-4-piperidone;
1-[4-fluorophenyl)aminocarbonylmethyl]-4-piperidone;
1-[(4-methylphenyl)aminocarbonylmethyl]-4-piperidone;
1-[(4-methoxyphenyl)aminocarbonylmethyl]-4-piperidone;
1-[(3-chlorophenyl)aminocarbonylmethyl]-4-piperidone;
1-[(4-hydroxyphenyl)aminocarbonylmethyl]-4-piperidone;
1-[(4-aminosulfonylphenyl)aminocarbonylmethyl]-4-piperidone;
1-[(3,4-methylenedioxyphenyl)aminocarbonylmethyl]-4-piperidone;
1-[(2,6-dichlorophenyl)aminocarbonylmethyl]-4-piperidone;
1-[(2,4,6-trimethylphenyl)aminocarbonylmethyl]-4-piperidone;
1-[(3,5-dimethoxyphenyl)aminocarbonylmethyl]-4-piperidone;
1-[(4-methylthiophenyl)aminocarbonylmethyl]-4-piperidone;
1-[(4-n-butylthiophenyl)aminocarbonylmethyl]-4-piperidone;
1-[(4-methylsulfinylphenyl)aminocarbonylmethyl]-4-piperidone;
1-[(4-n-butylsulfinylphenyl)aminocarbonylmethyl]-4-piperidone;
1-[(4-methylsulfonylphenyl)aminocarbonylmethyl]-4-piperidone;
1-[(4-n-butylsulfonylphenyl)aminocarbonylmethyl]-4-piperidone;
1-[(3-trifluoromethylphenyl)aminocarbonylmethyl]-4-piperidone;
1-[(2,6-dimethylphenylaminocarbonyl-1-n-pentyl]-4-piperidone;
1-[N-methyl-N-(2,6-dimethylphenylaminocarbonyl-1-n-pentyl]-4-piperidone;
1-[N-n-butyl-N-(2,6-dimethylphenylaminocarbonyl-1-n-pentyl]-4-piperidone;
[N-(methyl)aminocarbonylmethyl]-4-piperidone;
[N-(isopropyl)aminocarbonylmethyl]-4-piperidone;
[N-(n-butyl)aminocarbonylmethyl]-4-piperidone;
[N-(cyclopropyl)aminocarbonylmethyl]-4-piperidone;
[N-(cyclohexyl)aminocarbonylmethyl]-4-piperidone; or
[N-(cyclooctyl)aminocarbonylmethyl]-4-piperidone
in sufficient purity for use in this invention.

PREPARATION D

Preparation of
4-{[2-(1,4-benzodioxan-2-yl)-2-hydroxyethyl]amino}piperidine (Compound of formula E)

(a) In a manner similar to that described in Subpart (a) of Preparation C, but substituting 2-(1,4-benzodioxan-2-yl)-2-epoxide for the starting chloride and 4-aminopiperidine for the piperidone and refluxing for 6 hr rather than two hrs, one obtains the corresponding compound of formula E, namely 4-{[2-(1,4-benzodioxan-2-yl)-2-hydroxyethyl]amino}piperidine.

(b) Repeating the above procedure [Subpart (a)] in a similar manner and substituting a stoichiometrically equivalent amount of:
2-(6-methyl-1,4-benzodioxan-2-yl)-2-epoxide;
2-(6-n-butyl-1,4-benzodioxan-2-yl)-2-epoxide;
2-(6-methoxy-1,4-benzodioxan-2-yl)-2-epoxide;
2-(6-n-butoxy-1,4-benzodioxan-2-yl)-2-epoxide;
2-(6-chloro-1,4-benzodioxan-2-yl)-2-epoxide;
2-(6-bromo-1,4-benzodioxan-2-yl)-2-epoxide;
2-(7-methyl-1,4-benzodioxan-2-yl)-2-epoxide;
2-(7-methoxy-1,4-benzodioxan-2-yl)-2-epoxide;
2-(7-n-butoxy-1,4-benzodioxan-2-yl)-2-epoxide;
2-(7-chloro-1,4-benzodioxan-2-yl)-2-epoxide;

2-(6,7-dimethyl-1,4-benzodioxan-2-yl)-2-epoxide;
2-(6,7-dichloro-1,4-benzodioxan-2-yl)-2-epoxide;
2-(5,6,7-trichloro-1,4-benzodioxan-2-yl)-2-epoxide;
2-(5-methyl-6-chloro-7-methoxy-1,4-benzodioxan-2-yl)-2-epoxide;
2-(5,6,7,8-tetrabromo-1,4-benzodioxan-2-yl)-2-epoxide;
2-(5,8-dimethyl-6,7-dichloro-1,4-benzodioxan-2-yl)-2-epoxide;
2-(6-trifluoromethyl-1,4-benzodioxan-2-yl)-2-epoxide;
2-(6-methylthio-1,4-benzodioxan-2-yl)-2-epoxide;
2-(6-methylsulfinyl-1,4-benzodioxan-2-yl)-2-epoxide;
2-(6-methylsulfonyl-1,4-benzodioxan-2-yl)-2-epoxide;
2-(6-n-butylthio-1,4-benzodioxan-2-yl)-2-epoxide;
2-(6-n-butylsulfinyl-1,4-benzodioxan-2-yl)-2-epoxide;
or
2-(6-n-butylsulfonyl-1,4-benzodioxan-2-yl)-2-epoxide
for d,l-2-(1,4-benzodioxan-2-yl)-2-epoxide there are obtained the following piperidines:
4-{[2-(6-methyl-1,4-benzodioxan-2-yl)-2-hydroxyethyl]amino}piperidine;
4-{[2-(6-n-butyl-1,4-benzodioxan-2-yl)-2-hydroxyethyl]amino}piperidine;
4-{[2-(6-methoxy-1,4-benzodioxan-2-yl)-2-hydroxyethyl]amino}piperidine;
4-{[2-(6-n-butoxy-1,4-benzodioxan-2-yl)-2-hydroxyethyl]amino}piperidine;
4-{[2-(6-chloro-1,4-benzodioxan-2-yl)-2-hydroxyethyl]amino}piperidine;
4-{[2-(6-bromo-1,4-benzodioxan-2-yl)-2-hydroxyethyl]amino}piperidine;
4-{[2-(7-methyl-1,4-benzodioxan-2-yl)-2-hydroxyethyl]amino}piperidine;
4-{[2-(7-methoxy-1,4-benzodioxan-2-yl)-2-hydroxyethyl]amino}piperidine;
4-{[2-(7-n-butoxy-1,4-benzodioxan-2-yl)-2-hydroxyethyl]amino}piperidine;
4-{[2-(7-chloro-1,4-benzodioxan-2-yl)-2-hydroxyethyl]amino}piperidine;
4-{[2-(6,7-dimethyl-1,4-benzodioxan-2-yl)-2-hydroxyethyl]amino}piperidine;
4-{[2-(6,7-dichloro-1,4-benzodioxan-2-yl)-2-hydroxyethyl]amino}piperidine;
4-{[2-(5,6,7-trichloro-1,4-benzodioxan-2-yl)-2-hydroxyethyl]amino}piperidine;
4-{[2-(5-methyl-6-chloro-7-methoxy-1,4-benzodioxan-2-yl)-2-hydroxyethyl]amino}piperidine;
4-{[2-(5,6,7,8-tetrabromo-1,4-benzodioxan-2-yl)-2-hydroxyethyl]amino}piperidine;
4-{[2-(5,8-dimethyl-6,7-dichloro-1,4-benzodioxan-2-yl)-2-hydroxyethyl]amino}piperidine;
4-{[2-(6-trifluoromethyl-1,4-benzodioxan-2-yl)-2-hydroxyethyl]amino}piperidine;
4-{[2-(6-methylthio-1,4-benzodioxan-2-yl)-2-hydroxyethyl]amino}piperidine;
4-{[2-(6-methylsulfinyl-1,4-benzodioxan-2-yl)-2-hydroxyethyl]amino}piperidine;
4-{[2-(6-methylsulfonyl-1,4-benzodioxan-2-yl)-2-hydroxyethyl]amino}piperidine;
4-{[2-(6-n-butylthio-1,4-benzodioxan-2-yl)-2-hydroxyethyl]amino}piperidine;
4-{[2-(6-n-butylsulfinyl-1,4-benzodioxan-2-yl)-2-hydroxyethyl]amino}piperidine; or
4-{[2-(6-n-butylsulfonyl-1,4-benzodioxan-2-yl)-2-hydroxyethyl]amino}piperidine.

(c) Repeating the above procedure [Subpart (a)] in a similar manner and substituting a stoichiometrically equivalent amount of one of the d,l-erythro-[2-(optionally substituted-1,4-benzodioxan-2-yl)]-2-epoxides of Preparation A [Subpart (b)] for [2-(1,4-benzodioxan-2-yl)]-2-epoxide, one obtains the corresponding d,l-erythro-4-{[2-(optionally substituted-1,4-benzodioxan-2-yl)-2-hydroxyethyl]amino}piperidine.

(d) Repeating the above procedure [Subpart (a)] in a similar manner and substituting a stoichiometrically equivalent amount of any one of the d,l-threo-[2-(optionally substituted-1,4-benzodioxan-2-yl)]-2-epoxides in Preparation A [Subpart (d)] for [2-(1,4-benzodioxan-2-yl)]-2-epoxide, one obtains the corresponding, d,l-threo-4-{[2-(optionally substituted 1,4-benzodioxan-2-yl)-2-hydroxyethyl]amino}-piperidine.

(e) Repeating the above procedure [Subpart (a)] in a similar manner and substituting a stoichiometrically equivalent amount of a mixture of any one of the d,l-erythro and d,l-threo-(optionally substituted 1,4-benzodioxan-2-yl)-2-epoxides of Preparation A [Subparts (e) or (f)] for [2-(1,4-benzodioxan-2-yl)]-2-epoxide, one obtains the corresponding mixture of d,l-erythro and d,l-threo-4-{[2-(optionally substituted-1,4-benzodioxan-2-yl)-2-hydroxyethyl]amino}piperidine in good yield.

PREPARATION D'

Preparation of Compounds of Formula A'

(a) Fifty g of bromomethyl 1,4-benzodioxan-2-yl ketone (prepared according to *J. Med. Chem.*, 13, 169 (1970) is stirred slowly in 1000 ml of ethanol. To this stirred solution is slowly added dropwise 20 g of sodium borohydride. The crude product is then treated with ammonia (20 g) in a sealed vessel at 100° C. and 600 psi for 24 hours. The resulting [2-(1,4-benzodioxan-2-yl)-2-hydroxyethyl]amine (15 g) is recovered as the hydrochloride salt from ethyl acetate/hexane.

(b) Repeating the above procedure in [Subpart (a)] in a similar manner and substituting a stoichiometrically equivalent of:
bromomethyl (6-methyl-1,4-benzodioxan-2-yl)ketone;
bromomethyl (6-n-butyl-1,4-benzodioxan-2-yl)ketone;
bromomethyl (6-methoxy-1,4-benzodioxan-2-yl)ketone;
bromomethyl (6-n-butoxy-1,4-benzodioxan-2-yl)ketone;
bromomethyl (6-chloro-1,4-benzodioxan-2-yl)ketone;
bromomethyl (7-methyl-1,4-benzodioxan-2-yl)ketone;
bromomethyl (7-methoxy-1,4-benzodioxan-2-yl)ketone;
bromomethyl (7-chloro-1,4-benzodioxan-2-yl)ketone;
bromomethyl (6,7-dichloro-1,4-benzodioxan-2-yl)ketone;
bromomethyl (6-methyl-7-chloro-1,4-benzodioxan-2-yl)ketone
bromomethyl (5,6,7-trichloro-1,4-benzodioxan-2-yl)ketone;
bromomethyl (5-methyl-6,7-dichloro-1,4-benzodioxan-2-yl)ketone
bromomethyl (5-methyl-6-chloro-7-methoxy-1,4-benzodioxan-2-yl)ketone
bromomethyl (5,8-dimethyl-6,7-dichloro-1,4-benzodioxan-2-yl)ketone
bromomethyl (5,6,7,8-tetrabromo-1,4-benzodioxan-2-yl)ketone;
bromomethyl (6-trifluoromethyl-1,4-benzodioxan-2-yl)ketone;
bromomethyl (6-methylthio-1,4-benzodioxan-2-yl)ketone;
bromomethyl (6-n-butylthio-1,4-benzodioxan-2-yl)ketone
bromomethyl (6-methylsulfinyl-1,4-benzodioxan-2-yl)ketone bromomethyl (6-n-butylsulfinyl-1,4-benzodioxan-2-yl)ketone;
bromomethyl (6-methylsulfonyl-1,4-benzodioxan-2-yl)ketone; or
bromomethyl (6-n-butylsulfonyl-1,4-benzodioxan-2-yl)ketone
for bromomethyl 1,4-benzodioxan-2-yl ketone, there are obtained the following amines:
4-[(6-methyl-1,4-benzodioxan-2-yl)-2-hydroxyethyl]amine;
4-[(6-n-butyl-1,4-benzodioxan-2-yl)-2-hydroxyethyl]amine;
4-[(6-methoxy-1,4-benzodioxan-2-yl)-2-hydroxyethyl]amine;
4-[(6-n-butoxy-1,4-benzodioxan-2-yl)-2-hydroxyethyl]amine;
4-[(6-chloro-1,4-benzodioxan-2-yl)-2-hydroxyethyl]amine;
4-[(7-methyl-1,4-benzodioxan-2-yl)-2-hydroxyethyl]amine;
4-[(7-methoxy-1,4-benzodioxan-2-yl)-2-hydroxyethyl]amine;
4-[(7-chloro-1,4-benzodioxan-2-yl)-2-hydroxyethyl]amine;
4-[(6,7-dichloro-1,4-benzodioxan-2-yl)-2-methyl]piperidine;
4-[(6-methyl-7-chloro-1,4-benzodioxan-2-yl)-2-methyl]piperidine;
4-[(5,6,7-trichloro-1,4-benzodioxan-2-yl)-2-methyl]piperidine;
4-[((5-methyl-6,7-dichloro-1,4-benzodioxan-2-yl)-2-methyl]piperidine;
4-[(5-methyl-6-chloro-7-methoxy-1,4-benzodioxan-2-yl)-2-hydroxyethyl]amine;
4-[(5,8-dimethyl-6,7-dichloro-1,4-benzodioxan-2-yl)-2-hydroxyethyl]amine;
4-[(5,6,7,8-tetrabromo-1,4-benzodioxan-2-yl)-2-hydroxyethyl]amine;
4-[(6-trifluoromethyl-1,4-benzodioxan-2-yl)-2-hydroxyethyl]amine;
4-[(6-methylthio-1,4-benzodioxan-2-yl)-2-hydroxyethyl]amine;
4-[(6-n-butylthio-1,4-benzodioxan-2-yl)-2-hydroxyethyl]amine;
4-[(6-methylsulfinyl-1,4-benzodioxan-2-yl)-2-hydroxyethyl]amine;
4-[(6-n-butylsulfinyl-1,4-benzodioxan-2-yl)-2-hydroxyethyl]amine;
4-[(6-methylsulfonyl-1,4-benzodioxan-2-yl)-2-hydroxyethyl]amine; or
4-[(6-n-butylsulfonyl-1,4-benzodioxan-2-yl)-2-hydroxyethyl]amine.

PREPARATION E

Preparation of Compounds of Formula J (a) Fifty g of [2-(1,4-benzodioxan-2-yl)-2-hydroxyethyl]amine and 85 g of piperidone HCl (ALDRICH) are dissolved in 1000 ml of ethanol. Sodium cyanoborohydride (75 g) is added, and after stirring at ambient conditions overnight (about 16 hr) the mixture is cooled and evaporated. The product is recovered by extraction with methylene chloride to yield 4-{[2-(1,4-benzodioxan-2-yl)-2-hydroxyethyl]amino}piperidine. This material is of sufficient purity to use in this invention.

(b) Repeating the above procedure in [Subpart (a)] in a similar manner and substituting a stoichiometrically equivalent amount of:

[2-(6-methyl-1,4-benzodioxan-2-yl)-2-hydroxyethyl]amine;
[2-(6-n-butyl-1,4-benzodioxan-2-yl)-2-hydroxyethyl]amine;
[2-(6-methoxy-1,4-benzodioxan-2-yl)-2-hydroxyethyl]amine;
[2-(6-n-butoxy-1,4-benzodioxan-2-yl)-2-hydroxyethyl]amine;
[2-(6-chloro-1,4-benzodioxan-2-yl)-2-hydroxyethyl]amine;
[2-(7-methyl-1,4-benzodioxan-2-yl)-2-hydroxyethyl]amine;
[2-(7-methoxy-1,4-benzodioxan-2-yl)-2-hydroxyethyl]amine;
[2-(7-chloro-1,4-benzodioxan-2-yl)-2-hydroxyethyl]amine;
[2-(6,7-dichloro-1,4-benzodioxan-2-yl)-2-hydroxyethyl]amine;
[2-(6-methyl-7-chloro-1,4-benzodioxan-2-yl)-2-hydroxyethyl]amine;
[2-(5,6,7-trichloro-1,4-benzodioxan-2-yl)-2-hydroxyethyl]amine;
[2-(5-methyl-6,7-dichloro-1,4-benzodioxan-2-yl)-2-hydroxyethyl]amine;
[2-(5-methyl-6-chloro-7-methoxy-1,4-benzodioxan-2-yl)-2-hydroxyethyl]amine;
[2-(5,8-dimethyl-6,7-dichloro-1,4-benzodioxan-2-yl)-2-hydroxyethyl]amine;
[2-(5,6,7,8-tetrabromo-1,4-benzodioxan-2-yl)-2-hydroxyethyl]amine;
[2-(6-trifluoromethyl-1,4-benzodioxan-2-yl)-2-hydroxyethyl]amine;
[2-(6-methylthio-1,4-benzodioxan-2-yl)-2-hydroxyethyl]amine;
[2-(6-n-butylthio-1,4-benzodioxan-2-yl)-2-hydroxyethyl]amine;
[2-(6-methylsulfinyl-1,4-benzodioxan-2-yl)-2-hydroxyethyl]amine;
[2-(6-n-butylsulfinyl-1,4-benzodioxan-2-yl)-2-hydroxyethyl]amine;
[2-(6-methylsulfonyl-1,4-benzodioxan-2-yl)-2-hydroxyethyl]amine; or
[2-(6-n-butylsulfinyl-1,4-benzodioxan-2-yl)-2-hydroxyethyl]amine for [2-(1,4-benzodioxan-2-yl)-2-hydroxyethyl]amine, there are obtained the following piperidines:
4-{[2-(6-methyl-1,4-benzodioxan-2-yl)-2-hydroxyethyl]amino}piperidine;
4-{[2-(6-n-butyl-1,4-benzodioxan-2-yl)-2-hydroxyethyl]amino}piperidine;
4-{[2-(6-methoxy-1,4-benzodioxan-2-yl)-2-hydroxyethyl]amino}piperidine;
4-{[2-(6-n-butoxy-1,4-benzodioxan-2-yl)-2-hydroxyethyl]amino}piperidine;
4-{[2-(6-chloro-1,4-benzodioxan-2-yl)-2-hydroxyethyl]amino}piperidine;
4-{[2-(7-methyl-1,4-benzodioxan-2-yl)-2-hydroxyethyl]amino}piperidine;
4-{[2-(7-methoxy-1,4-benzodioxan-2-yl)-2-hydroxyethyl]amino}piperidine;
4-{[2-(7-chloro-1,4-benzodioxan-2-yl)-2-hydroxyethyl]amino}piperidine;
4-{[2-(6,7-dichloro-1,4-benzodioxan-2-yl)-2-hydroxyethyl]amino}piperidine;
4-{[2-(6-methyl-7-chloro-1,4-benzodioxan-2-yl)-2-hydroxyethyl]amino}piperidine;
4-{[2-(5,6,7-trichloro-1,4-benzodioxan-2-yl)-2-hydroxyethyl]amino}piperidine;

4-{[2-(5-methyl-6,7-dichloro-1,4-benzodioxan-2-yl)-2-hydroxyethyl]amino}piperidine;

4-{[2-(5-methyl-6-chloro-7-methoxy-1,4-benzodioxan-2-yl)-2-hydroxyethyl]amino}piperidine;

4-{[2-(5,8-dimethyl-6,7-dichloro-1,4-benzodioxan-2-yl)-2-hydroxyethyl]amino}piperidine;

4-{[2-(5,6,7,8-tetrabromo-1,4-benzodioxan-2-yl)-2-hydroxyethyl]amino}piperidine;

4-{[2-(6-trifluoromethyl-1,4-benzodioxan-2-yl)-2-hydroxyethyl]amino}piperidine;

4-{[2-(6-methylthio-1,4-benzodioxan-2-yl)-2-hydroxyethyl]amino}piperidine;

4-{[2-(6-n-butylthio-1,4-benzodioxan-2-yl)-2-hydroxyethyl]amino}piperidine;

4-{[2-(6-methylsulfinyl-1,4-benzodioxan-2-yl)-2-hydroxyethyl]amino}piperidine;

4-{[2-(6-n-butylsulfinyl-1,4-benzodioxan-2-yl)-2-hydroxyethyl]amino}piperidine;

4-{[2-(6-methylsulfonyl-1,4-benzodioxan-2-yl)-2-hydroxyethyl]amino}piperidine; or 4-{[2-(6-n-butylsulfonyl-1,4-benzodioxan-2-yl)-2-hydroxyethyl]amino}piperidine.

EXAMPLE 1

Preparation of 4-{[2-(1,4-benzodioxan-2-yl)-2-hydroxyethyl]amino}-1-[(2,6-dimethylphenyl)aminocarbonylmethyl]piperidine (Reaction Sequence 1)

(a) The [(2,6-dimethylphenyl)aminocarbonylmethyl]chloride from Preparation B [Subpart (a)] (12.9 g, 65 mmoles) and 4-{[2-(1,4-benzodioxan-2-yl)-2-hydroxyethyl]amino}piperidine from Preparation D [Subpart (a)] (15 g, 65 mmoles) are mixed in 100 ml of dimethylformamide. The mixture is stirred at 65° C. to dissolve the components, and then at 90° C. overnight. The entire mixture is added to water and acidified with hydrochloric acid. The resulting homogeneous mixture is washed with ether, and then made basic with ammonia, and extracted with three portions of methylene chloride. The methylene chloride extracts, which contained the product, are washed with water twice, and then evaporated to 28 g of an oil. The oil is purified by chromatography using 500 g of silica gel with 5% methanol in methylene chloride. The 20 g of yellow oil which are obtained are dissolved in methanol and crystallized by the addition of hydrochloric acid. Precipitation is completed by addition of ether and 16 g of the product, 4-{[2-(1,4-benzodioxan-2-yl)-2-hydroxyethyl]amino}-1-[(2,6-dimethylphenyl)aminocarbonylmethyl]piperidine, is obtained as the dihydrochloride.

Because the 4-{[2-(1,4-benzodioxan-2-yl)-2-hydroxyethyl]amino}piperidine from Preparation D has undefined stereochemistry at the carbon atom at the 2 ring position, this compound and the substituted compounds of Subparts (b), (c) and (d) below are obtained as a mixture of the d,l-erythro and d,l-threo forms.

(b) Similarly, proceeding as in Subpart (a) above but substituting a stoichiometrically equivalent amount of any one of the optionally substituted chloride compounds prepared in Preparation C above for 1-[(2,6-dimethylphenyl)aminocarbonylmethyl]chloride, there is obtained the corresponding 4-{[2-(1,4-benzodioxan-2-yl)-2-hydroxyethyl]amino}-1-[optionally substituted phenyl)aminocarbonylmethyl]piperidine.

Exemplary compounds are as follows:

4-{[2-(1,4-benzodioxan-2-yl)-2-hydroxyethyl]amino}-1-(phenylaminocarbonylmethyl)piperidine;

4-{[2-(1,4-benzodioxan-2-yl)-2-hydroxyethyl]amino}-1-[4-chlorophenyl)aminocarbonylmethyl]piperidine;

4-{[2-(1,4-benzodioxan-2-yl)-2-hydroxyethyl]amino}-1-[(4-methylphenyl)aminocarbonylmethyl]piperidine;

4-{[2-(1,4-benzodioxan-2-yl)-2-hydroxyethyl]amino}-1-[(4-methoxyphenyl)aminocarbonylmethyl]piperidine;

4-{[2-(1,4-benzodioxan-2-yl)-2-hydroxyethyl]amino}-1-[(4-bromophenyl)aminocarbonylmethyl]piperidine;

4-{[2-(1,4-benzodioxan-2-yl)-2-hydroxyethyl]amino}-1-[(3-chlorophenyl)aminocarbonylmethyl]piperidine;

4-{[2-(1,4-benzodioxan-2-yl)-2-hydroxyethyl]amino}-1-[(2,6-dichlorophenyl)aminocarbnylmethyl]piperidine;

4-{[2-(1,4-benzodioxan-2-yl)-2-hydroxyethyl]amino}-1-[(2,4,6-trimethylphenyl)aminocarbonylmethyl]piperidine;

4-{[2-(1,4-benzodioxan-2-yl)-2-hydroxyethyl]amino}-1-[(3,4,5-trimethoxyphenyl)aminocarbonylmethyl]piperidine;

4-{[2-(1,4-benzodioxan-2-yl)-2-hydroxyethyl]amino}-1-[(4-methylthiophenyl)aminocarbonylmethyl]piperidine;

4-{[2-(1,4-benzodioxan-2-yl)-2-hydroxyethyl]amino}-1-[(4-ethylthiophenyl)aminocarbonylmethyl]piperidine;

4-{[2-(1,4-benzodioxan-2-yl)-2-hydroxyethyl]amino}-1-[(4-methylsulfinylphenyl)aminocarbonylmethyl]piperidine;

4-{[2-(1,4-benzodioxan-2-yl)-2-hydroxyethyl]amino}-1-[(4-n-propylsulfinylphenyl)aminocarbonylmethyl]piperidine;

4-{[2-(1,4-benzodioxan-2-yl)-2-hydroxyethyl]amino}-1-[(4-trifluoromethylphenyl)aminocarbonylmethyl]piperidine;

4-{[2-(1,4-benzodioxan-2-yl)-2-hydroxyethyl]amino}-1-4-[[(2-chloro-5-methylphenyl)aminocarbonylmethyl]piperidine;

4-{[2-(1,4-benzodioxan-2-yl)-2-hydroxyethyl]amino}-1-[(3,5-difluorophenyl)aminocarbonylmethyl]piperidine;

4-{[2-(1,4-benzodioxan-2-yl)-2-hydroxyethyl]amino}-1-[(2,6-diethoxyphenyl)aminocarbonylmethyl]piperidine;

4-{[2-(1,4-benzodioxan-2-yl)-2-hydroxyethyl]amino}-1-[(3-bromo-4-ethylphenyl)aminocarbonylmethyl]piperidine;

4-{[2-(1,4-benzodioxan-2-yl)-2-hydroxyethyl]amino}-1-[(4-n-butylphenyl)aminocarbonylmethyl]piperidine; and 4-{[2-(1,4-benzodioxan-2-yl)-2-hydroxyethyl]amino}-1-[(4-isobutylphenyl)aminocarbonylmethyl]piperidine.

Additional exemplary compounds where $R^5$ and $R^6$ are each hydrogen, or alkyl, i.e., methyl or n-butyl may be prepared by replacement of the phenyl aminocarbonylmethyl chloride derivative by the appropriately substituted chlorides described in Preparation B, Subparts (b), (c), (d) and (e). One representative compound is 4-{[2-(1,4-benzodioxan-2-yl)-2-hydroxyethyl]amino}-1-[N-n-butyl-N-(2,6-dimethylphenyl)aminocarbonyl-1-n-pentyl]piperidine.

(c) Similarly, proceeding as in Subpart (a) above but substituting a stoichiometrically equivalent of any one of the optionally substituted piperidine compounds described in Preparation D [Subpart (b)] above for 4-[2-

4-{2-(6-methoxy-1,4-benzodioxan-2-yl)-2-hydroxyethyl]amino}-1-[(2,6-dimethylphenyl)aminocarbonylmethyl]piperidine;

4-{[2-(6-chloro-1,4-benzodioxan-2-yl)-2-hydroxyethyl]amino}-1-[(2,6-dimethylphenyl)aminocarbonylmethyl]piperidine;

4-{[2-(7-methyl-1,4-benzodioxan-2-yl)-2-hydroxyethyl]amino}-1-[(2,6-dimethylphenyl)aminocarbonylmethyl]piperidine;

4-{[2-(7-methoxy-1,4-benzodioxan-2-yl)-2-hydroxyethyl]amino}-1-[(2,6-dimethylphenyl)aminocarbonylmethyl]piperidine;

4-{[2-(7-chloro-1,4-benzodioxan-2-yl)-2-hydroxyethyl]amino}-1-{(2,6-dimethylphenyl)aminocarbonylmethyl]piperidine; or 4-{[2-(6,7-dimethyl-1,4-benzodioxan-2-yl)-2-hydroxyethyl]amino}-1-[(2,6-dimethylphenyl)aminocarbonylmethyl]piperidine.

Additional exemplary compounds which may have the d,l-erythro form are described and named in Subparts (b), (c), (d) and (e) of this example.

(g) Similarly, proceeding as in Subpart (a) above substituting a stoichiometrically equivalent amount of optionally substituted d,l-threo-4-{[2-(1,4-benzodioxan-2-yl)-2-hydroxyethyl]amino}piperidine compounds described in Preparation D for 2-[(1,4-benzodioxan-2-yl)-2-hydroxyethyl]piperidine and also substituting a stoichiometrically equivalent amount of any one of the optionally substituted phenyl aminocarbonylmethyl chloride compounds described in Preparation B [Subpart (b)] above for 1-[(2,6-dimethylphenyl)aminocarbonylmethyl]chloride, there is obtained the corresponding d,l-threo-4-{[2-(optionally substituted-1,4-benzodioxan-2-yl)-2-hydroxyethyl]amino}-1-(optionally substituted phenyl)aminocarbonylmethyl]piperidine.

Additional exemplary compounds which may have the d,l-threo form are described and named in Subparts (b), (c), (d) (e), and (f) of this example.

(h) Similarly, proceeding as in Subpart (a) above substituting a stoichiometrically equivalent amount of a mixture of any one of the optionally substituted d,l-erythro and d,l-threo-4-{[2-(1,4-benzodioxan-2-yl)-2-hydroxyethyl]amino}piperidine compounds described in Preparation D for 4-{[2-(1,4-benzodioxan-2-yl)-2-hydroxyethyl]amino}piperidine and also substituting a stoichiometrically equivalent amount of any one of the optionally substituted phenyl aminocarbonylmethyl chloride compounds described in Preparation B [Subpart (b)] above for 1-[(2,6-dimethylphenyl)aminocarbonylmethyl]chloride, there is obtained the corresponding mixture of d,l-erythro and d,l-threo-4-{[2-(optionally substituted-1,4-benzodioxan-2-yl)-2-hydroxyethyl]amino}-1-[(optionally substituted phenyl)aminocarbonylmethyl]piperidine.

Additional exemplary mixtures containing both the d,l-erythro and d,l-threo form are described and named in Subparts (b), (c), (d), (e), and (f) of this example.

EXAMPLE 2

Preparation of
4-{[2-(1,4-benzodioxan-2-yl)-2-hydroxyethyl]amino}-1-[(2,6-dimethylphenyl)aminocarbonylmethyl]piperidine (Reaction Sequence 2)

(a) Substituting into the procedure of Example 1, 1-[(2,6-dimethylphenyl)aminocarbonylmethyl]-4-piperidone for the corresponding chloride and [2-(1,4-benzodioxan-2-yl)-2-hydroxyethyl]amine or amine hydrochloride, rather than the corresponding piperidine and adding 75 g of sodium cyanoborohydride, one obtains 4-{[2-(1,4-benzodioxan-2-yl)-2-hydroxyethyl]amino}-1-[(2,6-dimethylphenyl)aminocarbonylmethyl]piperidine compound.

Because the 4-{2-[1,4-benzodioxan-2-yl)-2-hydroxyethyl]amino}piperidine from Preparation B has undefined stereochemistry at the carbon atom at position 2 of the ring, this compound and the substituted compounds of Subparts (b), (c) and (d) below are obtained as a mixture of the d,l-erythro and d,l-threo forms.

(b) Similarly, proceeding as in Subpart (a) above but substituting a stoichiometrically equivalent amount of any one of the optionally substituted phenyl piperidine compounds described in Preparation B above for 1-[(2,6-dimethylphenyl)aminocarbonylmethyl]piperidine, there is obtained the corresponding 4-{[2-(1,4-benzodioxan-2-yl)-2-hydroxyethyl]amino}-1-[(optionally substituted phenyl)aminocarbonylmethyl]piperidine.

Exemplary compounds are described and named in Example 1 above.

(c) Similarly, proceeding as in Subpart (a) above of the Preparation but substituting stoichiometrically equivalent amount of any one of the 2-(optionally substituted 1,4-benzodioxan-2-yl)-2-epoxide compounds described in Preparation C, [Subpart (b)] above for [2-(1,4-benzodioxan-2-yl)-2-hydroxyethyl]amine, there is obtained the corresponding 4-{[2-(optionally substituted-1,4-benzodioxan-2-yl)-2-hydroxyethyl]amino}-1-[(2,6-dimethylphenyl)aminocarbonylmethyl]piperidine.

Exemplary compounds are described and named in Example 1 [Subpart (c)] above.

(d) Similarly, proceeding as in Subpart (a) above of this Preparation but substituting a stoichiometrically equivalent amount of any one of the optionally substituted phenyl piperidine compounds described in Preparation C above for 1-[(2,6-dimethylphenyl)aminocarbonylmethyl]piperidine, and substituting a stoichiometrically equivalent amount of any one of the 2-(optionally substituted 1,4-benzodioxan-2-yl)-2-epoxides described in Preparation A above for {[2-(1,4-benzodioxan-2-yl)-2-hydroxyethyl]amino}chloride, there is obtained the corresponding 4-{[2-(optionally substituted-1,4-benzodioxan-2-yl)-2-hydroxyethyl]amino}-1-[(optionally substituted phenyl)aminocarbonylmethyl]piperidine.

Exemplary compounds are described and named in Example 1 [Subpart (d)] above.

(e) Similarly, proceeding as in Subpart (a) above but substituting a stoichiometrically equivalent amount of optionally substituted d,l-erythro-[2-(1,4-benzodioxan-2-yl)-2-hydroxyethyl]chloride, and also substituting a stoichiometrically equivalent amount of any one of the optionally substituted phenyl piperidine compounds described in Preparation C above for 1-[(2,6-dimethylphenyl)aminocarbonylmethyl]piperidine, there is obtained the corresponding d,l-erythro-4-{[2-(optionally substituted-1,4-benzodioxan-2-yl)-2-hydroxyethyl]amino}-1-[(optionally substituted phenyl)aminocarbonylmethyl]piperidine.

Exemplary compounds of the d,l-erythro form are described and named in Example 1, Subparts (b), (c) and (d) above.

(f) Similarly, proceeding as in Subpart (a) above but substituting a stoichiometrically equivalent amount of optionally substituted d,l-threo-[2-(1,4-benzodioxan-2-yl)-2-hydroxyethyl]piperidine compounds described in (1,4-benzodioxan-2-yl)-2-hydroxyethyl]piperidine, there is obtained the corresponding 1-{[2-(optionally substituted-1,4-benzodioxan-2-yl)-2-hydroxyethyl]amino}-1-[(2,6-dimethylphenyl)aminocarbonylmethyl]piperidine.

Exemplary compounds include the following:

4-{[2-(6-methyl-1,4-benzodioxan-2-yl)-2-hydroxyethyl]amino}-1-[(2,6-dimethylphenyl)aminocarbonylmethyl]piperidine;

4-{[2-(6-methoxy-1,4-benzodioxan-2-yl)-2-hydroxyethyl]amino}-1-[(2,6-dimethylphenyl)aminocarbonylmethyl]piperidine;

4-{[2-(6-chloro-1,4-benzodioxan-2-yl)-2-hydroxyethyl]amino}-1-[(2,6-dimethylphenyl)aminocarbonylmethyl]piperidine;

4-{[2-(7-methyl-1,4-benzodioxan-2-yl)-2-hydroxyethyl]amino}-1-[(2,6-dimethylphenyl)aminocarbonylmethyl]piperidine;

4-{[2-(7-methoxy-1,4-benzodioxan-2-yl)-2-hydroxyethyl]amino}-1-[(2,6-dimethylphenyl)aminocarbonylmethyl]piperidine;

4-{[2-(7-chloro-1,4-benzodioxan-2-yl)-2-hydroxyethyl]amino}-1-[(2,6-dimethylphenyl)aminocarbonylmethyl]piperidine; or 4-{[2-(6,7-dimethyl-1,4-benzodioxan-2-yl)-2-hydroxyethyl]amino}-1-[(2,6-dimethylphenyl)aminocarbonylmethyl]piperidine.

(d) Similarly, proceeding as in [Subpart (a)] above but substituting a stoichiometrically equivalent amount of any one of the optionally substituted chloride compounds described in Preparation B [Subpart (b)] above for 1-[(2,6-dimethylphenyl)aminocarbonylmethyl]chloride and also substituting a stoichiometrically equivalent amount of any one of the substituted piperidine compounds described in Preparation D [(Subpart (b)] above for 2-[(1,4-benzodioxan-2-yl)-2-hydroxyethyl]piperidine, there is obtained the corresponding 4-{[2-(optionally substituted-1,4-benzodioxan-2-yl)-2-hydroxyethyl]amino}-1-[(optionally substituted phenyl)aminocarbonylmethyl]piperidine.

Exemplary compounds are as follows:

4-{[2-(6-methyl-1,4-benzodioxan-2-yl)-2-hydroxyethyl]amino}-1-(phenylaminocarbonylmethyl)piperidine;

4-{[2-(6-chloro-1,4-benzodioxan-2-yl)-2-hydroxythyl]amino}-1-[(4-chlorophenyl)aminocarbonylmethyl]piperidine;

4-{[2-(6-methoxy-1,4-benzodioxan-2-yl)-2-hydroxyethyl]amino}-1-[(3-chlorophenyl)aminocarbonylmethyl]piperidine;

4-{[2-(6-methoxy-1,4-benzodioxan-2-yl)-2-hydroxyethyl]amino}-1-[(2,6-dichlorophenyl)aminocarbonylmethyl]piperidine;

4-{[2-(6-methoxy-1,4-benzodioxan-2-yl)-2-hydroxyethyl]amino}-1-[(2,4,6-trimethylphenyl)aminocarbonylmethyl]piperidine;

4-{[2-(6-methylthio-1,4-benzodioxan-2-yl)-2-hydroxyethyl]amino}-1-{(3,5-dimethoxyphenyl)aminocarbonylmethyl]piperidine;

4-{[2-(7-chloro-1,4-benzodioxan-2-yl)-2-hydroxyethyl]amino}-1-[(4-methylthiophenyl)aminocarbonylmethyl]piperidine;

4-{[2-(7-methyl-1,4-benzodioxan-2-yl)-2-hydroxyethyl]amino}-1-[(4-ethylthiophenyl)aminocarbonylmethyl]piperidine;

4-{[2-(7-methoxy-1,4-benzodioxan-2-yl)-2-hydroxyethyl]amino}-1-[4-methylsulfinylphenyl)aminocarbonylmethyl]piperidine;

4-{[2-(6-trifluoromethyl-1,4-benzodioxan-2-yl)-2-hydroxyethyl]amino}-1-[(4-n-butylsulfinylphenyl)aminocarbonylmethyl]piperidine;

4-{[2-(6-methyl-1,4-benzodioxan-2-yl)-2-hydroxyethyl]amino}-1-[(4-trifluoromethylphenyl)aminocarbonylmethyl]piperidine;

4-{[2-(6-methylsulfinyl-1,4-benzodioxan-2-yl-2-hydroxyethyl]amino}-1-[(2-chloro-5-methylphenyl)aminocarbonylmethyl]piperidine;

4-{[2-(6-methylsulfonyl-1,4-benzodioxan-2-yl)-2-hydroxyethyl]amino}-1-[(3,5-difluorophenyl)aminocarbonylmethyl]piperidine;

4-{[2-(6-n-butylsulfinyl-1,4-benzodioxan-2-yl)-2-hydroxyethyl]amino}-1-[(2,6-diethoxyphenyl)aminocarbonylmethyl]piperidine;

4-{[2-(6-methoxy-1,4-benzodioxan-2-yl)-2-hydroxyethyl]amino}-1-[(3-bromo-1-ethylphenyl)aminocarbonylmethyl]piperidine;

4-{[2-(6-methylthio-1,4-benzodioxan-2-yl)-2-hydroxyethyl]amino}-1-[(4-n-butylphenyl)aminocarbonylmethyl]piperidine;

4-{[2-(7-methoxy-1,4-benzodioxan-2-yl)-2-hydroxyethyl]amino}-1-[(4-isobutylphenyl)aminocarbonylmethyl]piperidine;

4-{[2-(6-n-butylthio-1,4-benzodioxan-2-yl)-2-hydroxyethyl]amino}-1-[(2,6-dimethylphenyl)aminocarbonylmethyl]piperidine;

4-{[2-(5-methyl-6,7-dichloro-1,4-benzodioxan-2-yl)-2-hydroxyethyl]amino}-1-[(2,6-dimethylphenyl)aminocarbonylmethyl]piperidine;

4-{[2-(5,6,7,8-tetrachloro-1,4-benzodioxan-2-yl)-2-hydroxyethyl]amino}-1-[(2,6-dimethylphenyl)aminocarbonylmethyl]piperidine;

4-{[2-(5-methyl-6-chloro-1,4-benzodioxan-2-yl)-2-hydroxyethyl]amino}-1-[(2,6-dimethylphenyl)aminocarbonylmethyl]piperidine;

4-{[2-(7-n-butylsulfinyl-1,4-benzodioxan-2-yl)-2-hydroxyethyl]amino}-1-[(2,6-dimethylphenyl)aminocarbonylmethyl]piperidine;

4-{[2-(7-n-butylsulfonyl-1,4-benzodioxan-2-yl)-2-hydroxyethyl]amino}-1-[(2,6-dimethylphenyl)aminocarbonylmethyl]piperidine; and 4-{[2-(6,7-dimethyl-1,4-benzodioxan-2-yl)-2-hydroxyethyl]amino}-1-[(2,6-dimethylphenyl)aminocarbonylmethyl]piperidine.

(e) Similarly, proceeding as in Subpart (a) above but substituting a stoichiometrically equivalent amount of optionally substituted d,l-erythro-2-[(1,4-benzodioxan-2-yl)-2-hydroxyethyl]piperidine compounds described above in Preparation D [Subpart (d)] for 2-[(1,4-benzodioxan-2-yl)-2-hydroxyethyl]piperidine, and also substituting a stoichiometrically equivalent amount of any one of the optionally substituted phenylchloride compounds described in Preparation B above for 4-[(2,6-dimethylphenyl)aminocarbonylmethyl]chloride, there is obtained the corresponding d,l-erythro-4-[2-(optionally substituted-1,4-benzodioxan-2-yl)-2-hydroxyethyl]-4-[(optionally substituted phenyl)aminocarbonylmethyl]piperidine.

(f) Similarly, proceeding as in Subpart (a) above, but substituting the appropriate 2-(optionally substituted 1,4-benzodioxan-2-yl)-2-epoxide for 2-(1,4-benzodioxan-2-yl)-2-epoxide, the following exemplary compounds are prepared:

4-{[2-(6-methyl-1,4-benzodioxan-2-yl)-2-hydroxyethyl]amino}-1-[(2,6-dimethylphenyl)aminocarbonylmethyl]piperidine;

Preparation D above for [2-(1,4-benzodioxan-2-yl)-2-hydroxyethyl]piperidine, and also substituting a stoichiometrically equivalent amount of any one of the optionally substituted phenylaminocarbonyl chloride compounds described in Preparation B above for 1-[(2,6-dimethylphenyl)aminocarbonylmethyl]chloride, there is obtained the corresponding d,l-threo-4-{[2-(optionally substituted-1,4-benzodioxan-2-yl)-2-hydroxyethyl]amino}-1-[(optionally substituted phenyl)aminocarbonylmethyl]piperidine.

(g) Exemplary compounds of the d,l-threo form are described and named in Example 1, Subparts (b), (c) and (d) above.

EXAMPLE 2A

Preparation of 4-{[2-(1,4-benzodioxan-2-yl)-2-hydroxyethyl]amino}-1-[(2,6-dimethylphenyl)aminocarbonylmethyl]piperidine.

(Reaction Sequence 2A)

(a) 1-[(2,6-dimethylphenyl) aminocarbonylmethyl]-4-piperidone (5 g) is treated in 50 ml of methanol with about 0.5 g of No. 3A molecular sieves, 3 ml of benzylamine and 2 grams of sodium cyanoborohydride. The mixture is stirred in a nitrogen atmosphere for 2.5 hrs and the solvent removed. The residue is slowly dissolved in ethylacetate and dilute hydrochloric acid is added. When the foaming is complete, the mixture is shaken and the layers are separated.

The aqueous layer is treated with base and extracted with methylene chloride dried and reduced to dryness. The residue is dissolved in ethyl acetate and hexane is added until the solution is cloudy. The intermediate product crystallizes slowly from this solvent, yield 3.0 g. The nuclear magnetic resonance spectrum is consistent with the structure.

The benzyl amine piperidine is then treated with 2-(1,4-benzodioxan-2-yl)-2-epoxide in toluene/methanol at reflux conditions for 6 hrs. The benzyl amine derivative of the title compound is recovered from ethyl acetate/hexane, yield 2.5 g, and subsequently dissolved in 100 ml of ethanol, treated with 0.3 g of 10% palladium-on-carbon and hydrogenated at 50 psi overnight (about 16 hours). The crude product is filtered, excess cold hydrochloric acid is added and the solvent is removed and the residue is triturated with diethyl ether. The product is filtered and dried in a desiccator, mp 158°–160° C. Infra-red, nuclear magnetic resonance and mass spectral analysis are consistent with the structure of 4-{[2-(1,4-benzodioxan-2-yl)-2-hydroxyethyl]amino}-1-[(2,6-dimethylphenyl)aminocarbonylmethyl]piperidine dihydrochloride.

Anal. for $C_{25}H_{35}Cl_2N_3O_4$: Calcd: C, 58.59; H, 6.88; N, 8.20. Found: C, 53.84; H, 7.25; N, 7.52.

(b) In a corresponding manner to that described in Example 2 [Subparts (b) to (g)] when a stoichiometrically equivalent amount of 1-[(optionally substituted phenyl)aminocarbonylmethyl]-4-piperidone is substituted for 1-[(2,6-dimethylphenyl)aminocarbonylmethyl]-4-piperidone and 4-[2-(optionally substituted-1,4-benzodioxan-2-yl)-2-hydroxyethyl]amine or amine hydrochloride [d,l-erythro-d,l-threo- or mixtures therof], there is obtained the corresponding d,l-erthyro-, d,l-threo-4-{[2-(optionally substituted-1,4-benzodioxan-2-yl)-2-hydroxyethyl]amine{-1-[(optionally substituted)aminocarbonylmethyl (or lower alkyl)]piperidine or mixtures thereof, respectively.

EXAMPLE 3

Preparation of 4-{[2-(1,4-benzodioxan-2-yl)-2-hydroxyethyl]amino}-1-[(2,6-dimethylphenyl)aminocarbonylmethyl]piperidine (Reaction Sequence 3)

(a) The 1-[(2,6-dimethylphenyl)aminocarbonylmethyl]chloride of Preparation B (12.6 g) and 4-{[2-(1,4-benzodioxan-2-yl)-2-carbonylmethyl]amino}piperidine (Compound J) (15 g) are mixed in 105 ml of dimethylformamide. The mixture is stirred at about 65°–70° C. to dissolve the components, and about 90° C. overnight. The mixture is added to water and ice (about 100 ml), acidified with hydrochloric acid, washed with ether, made basic with ammonia and extracted with three 100 ml portions of methylene chloride. The methylene chloride extracts are combined, washed with two 50 ml portions of water and evaporated to a tan oil weighing 27 g, which is purified by chromatography using 500 g of silica gel using 5% methanol/methylene chloride as eluant. The 19 g of yellow oil which are obtained are dissolved in methanol and crystallized using ether to produce 15 g of 4-{[2-(1,4-benzodioxan-2-yl)-2-hydroxyethyl]amino}-1-[(2,6-dimethylphenyl)aminocarbonylmethyl]piperidine.

Because the 2-(1,4-benzodioxan-2-yl)-2-epoxide from Preparation A has undefined stereochemistry at the carbon atom at position 2 of the ring, this compound and the substituted compounds of Subparts (b), (c) and (d) below are obtained as a mixture of the d,l-erythro and d,l-threo forms.

(b) Similarly, proceeding as in Subpart (a) above but substituting a stoichiometrically equivalent amount of any one of the optionally substituted phenyl, cycloalkyl or alkyl piperidine compounds described in Preparation B above for 1-[(2,6-dimethylphenyl)aminocarbonylmethyl]piperidine, there is obtained the corresponding 4-{[2-(1,4-benzodioxan-2-yl)-2-hydroxyethyl]amino}-1-[(optionally substituted phenyl, cycloalkyl or lower alkyl)aminocarbonylmethyl]piperidine.

Exemplary compounds are described and named in Example 1 [Subpart (b)] above.

(c) Similarly, proceeding as in Subpart (a) above but substituting a stoichiometrically equivalent amount of any one of the optionally substituted [2-(1,4-benzodioxan-2-yl-2-hydroxyethyl]amine compounds described in Preparation C [Subpart (b)] above for [2-(1,4-benzodioxan-2-yl)-2-hydroxyethyl]amine, there is obtained the corresponding 4-{[2-(optionally substituted-1,4-benzodioxan-2-yl)-2-hydroxyethyl]amino}-1-[(2,6-dimethylphenyl)aminocarbonylmethyl]piperidine.

Exemplary compounds are described in Example 1 [Subpart (c)] above.

(d) Similarly, proceeding as in Subpart (a) above but substituting a stoichiometrically equivalent amount of any one of the optionally substituted phenyl, cycloalkyl or lower alkyl piperidine compounds described in Preparation C above for 4-[(2,6-dimethylphenyl)aminocarbonylmethyl]piperidone, and substituting a stoichiometrically equivalent amount of any one of the 2-(optionally substituted 1,4-benzodioxan-2-yl)-2-epoxides described in Preparation A above for {[2-(1,4-benzodioxan-2-yl)-2-hydroxyethyl]amine}-chloride, there is obtained the corresponding 4-{[2-(optionally substituted-1,4-benzodioxan-2-yl)-2-hydroxyethyl]amino}-1-[(optionally substituted phenyl, cycloalkyl or lower alkyl)aminocarbonylmethyl]piperidine.

Exemplary compounds are described and named in Example 1 [Subpart (d)] above.

(e) Similarly, proceeding as in Subpart (a) above but substituting a stoichiometrically equivalent amount of d,l-erythro-[2-(optionally substituted 1,4-benzodioxan-2-yl)-2-hydroxyethyl]chloride, and also substituting a stoichiometrically equivalent amount of any one of the optionally substituted phenyl piperidine compounds described in Preparation C above for 1-[(2,6-dimethylphenyl)aminocarbonylmethyl]piperidine, there is obtained the corresponding d,l-erythro-4-{[2-(optionally substituted-1,4-benzodioxan-2-yl)-2-hydroxyethyl]amino}-1-[(optionally substituted phenyl)aminocarbonylmethyl]piperidine.

Exemplary compounds of the d,l-erythro form are described in Example 1, Subparts (b), (c) and (d) above.

(f) Similarly, proceeding as in Subpart (a) above but substituting a stoichiometrically equivalent amount of the d,l-threo-2-[(optionally substituted 1,4-benzodioxan-2-yl)-2-hydroxyethyl]piperidine compounds described in Preparation D above for [2-(1,4-benzodioxan-2-yl)-2-hydroxyethyl]piperidine, and also substituting a stoichiometrically equivalent amount of any one of the substituted phenylaminocarbonylmethyl chloride compounds described in Preparation B [Subpart (b)] above for 1-[(2,6-dimethylphenyl)aminocarbonylmethyl]chloride, there is obtained the corresponding d,l-threo-4-{[2-(optionally substituted-1,4-benzodioxan-2-yl)-2-hydroxyethyl]amino}-1-[(optionally substituted phenyl)aminocarbonylmethyl]piperidine.

(g) Exemplary compounds of the d,l-threo form are described and named in Example 1, Subparts (b), (c) and (d) above.

EXAMPLE 4

Preparation of 4-{[2-(1,4-Benzodioxan-2-yl)2-hydroxyethyl]amino}-1-[(3-phenylpropenoyl)]piperidine (Reaction Sequence 4)

(a) [2-(1,4-Benzodioxan-2-yl)-2-hydroxyethyl]amine (formula A') (50 g), 1-(3-phenylpropenoyl)piperidone (formula K) (75 g) and sodium cyanoborohydride (60 g) in 1000 ml of methanol are combined and stirred at ambient temperature for two days. The solvent is removed in vacuum, and the residue is taken up in 2000 ml of ethyl acetate and 500 ml of water. The ethyl acetate layer is dried using anhydrous sodium sulfate, concentrated in vacuum, and the residue is dissolved in methanol and heated with excess hydrochloric acid in diethyl ether. The hydrochloride salt of 4-}[2-(1,4-benzodioxan-2-yl)-2-hydroxyethyl]amino}-1-[3-phenylpropenoyl]piperidine precipitates from the solution.

(b) Exemplary compounds of formula I are produced by the replacement of the compound of formula A with its substituted analogs and also by the replacement of the compound of formula K of Reaction Sequence 4 with its substituted analogs. Additional exemplary compounds of formula I are described and named below.

Proceeding as in subpart (a) above of this Preparation but substituting a stoichiometrically equivalent amount of 1-[3-(2-chlorophenyl)propenoyl]piperidone;
1-[3-(4-methylphenyl)propenoyl]piperidone;
1-[3-(4-methoxyphenyl)propenoyl]piperidone;
1-[3-(2,6-dimethylphenyl)propenoyl]piperidone;
1-[3-(2,6-dichlorophenyl)propenoyl]piperidone; or
1-(3,4,5-trimethoxyphenylpropenoyl)piperidone for 1-(3-phenylpropenoyl)piperidone, there is obtained the corresponding 4-{[2-(1,4-benzodioxan-2-yl)-2-hydroxyethyl]amino}-1-[3-(2-chlorophenyl)propenoyl]piperidine;
4-{[2-(1,4-benzodioxan-2-yl)-2-hydroxyethyl]amino}-1-[3-(4-methylphenyl)propenoyl]piperidine;
4-{[2-(1,4-benzodioxan-2-yl)-2-hydroxyethyl]amino}-1-[3-(4-methoxyphenyl)propenoyl]piperidine;
4-{[2-(1,4-benzodioxan-2-yl)-2-hydroxyethyl]amino}-1-[3-(2,6-dimethylphenyl)propenoyl]piperidine;
4-{[2-(1,4-benzodioxan-2-yl)-2-hydroxyethyl]amino}-1-[3-(2,6-dichlorophenyl)propenoyl]piperidine; or
4-{[2-(1,4-benzodioxan-2-yl)-2-hydroxyethyl]amino}-1-[3-(3,4,5-trimethoxyphenyl)propenoyl]piperidine (d,l-erythro-mono HCl, mp 201°–202° C.) as the hydrochloride salt.

EXAMPLE 4A

Preparation of 4-{[2-(1,4-benzodioxan-2-yl)-2-hydroxyethyl]amino}-1-(benzoyl)piperidine (Reaction Sequence 4A)

(a) [2-(1,4-Benzodioxan-2-yl)-2-hydroxyethyl]amine (Formula A') (50 g) and 1-(benzoyl)-4-piperidone (prepared from benzoyl chloride and 4-piperidone) (75 g) and sodium cyanoborohydride (60 g) in 1000 ml of methanol are combined and stirred at ambient temperature for 2 days. The solvent is removed in vacuum and the residue is taken up in 2 liters of ethylacetate and 500 ml of water. The ethyl acetate layer is dried using anhydrous sodium sulfate, concentrated in vacuum, and the residue is dissolved in methanol and treated with excess hydrochloric acid in diethyl ether. The hydrochloride salt precipitates from the solution, 4-{[2-(1,4-benzodioxan-2-yl-2-hydroxyethyl]amino}-1-(benzoyl)piperidine.

(b) Similarly, proceeding as in Subpart (a) above but substituting a stoichiometrically equivalent amount of
1-(4-methylbenzoyl)-4-piperidone;
1-(4-n-butylbenzoyl)-4-piperidone;
1-(4-methoxybenzoyl)-4-piperidone;
1-(4-n-butoxybenzoyl)-4-piperidone;
1-(4-chlorobenzoyl)-4-piperidone;
1-(4-fluorobenzoyl)-4-piperidone;
1-(4-trifluoromethylbenzoyl)-4-piperidone;
1-(2,6-dimethylbenzoyl)-4-piperidone;
1-(2,6-methoxybenzoyl)-4-piperidone;
1-(3,4-methylenedioxybenzoyl)-4-piperidone;
1-(2,6-dichlorobenzoyl)-4-piperidone;
1-(3,4,5-trimethoxybenzoyl)-4-piperidone;
1-(2-phenylacetyl)-4-piperidone;
1-(5-phenyl-n-pentanoyl)-4-piperidone;
1-(acetyl)-4-piperidone;
1-(propionyl)-4-piperidone;
1-(n-butanoyl)-4-piperidone;
1-(isobutanoyl)-4-piperidone;
1-(n-pentanoyl)-4-piperidone;
1-(cyclopropylcarbonyl)-4-piperidone;
1-(2-methylcyclopentylcarbonyl)-4-piperidone; or
1-(cyclohexylcarbonyl)-4-piperidone
1-(benzoyl)-4-piperidone, there are obtained the corresponding compounds:
4-{[2-(1,4-benzodioxan-2-yl)-2-hydroxyethyl]amino}-1-(4-methylbenzoyl)piperidine;
4-{[2-(1,4-benzodioxan-2-yl)-2-hydroxyethyl]amino}-1-(4-n-butylbenzoyl)piperidine;

4-{[2-(1,4-benzodioxan-2-yl)-2-hydroxyethyl]amino}-1-(4-methoxybenzoyl)piperidine;
4-{[2-(1,4-benzodioxan-2-yl)-2-hydroxyethyl]amino}-1-(4-n-butoxybenzoyl)piperidine;
4-{[2-(1,4-benzodioxan-2-yl)-2-hydroxyethyl]amino}-1-(4-chlorobenzoyl)piperidine;
4-{[2-(1,4-benzodioxan-2-yl)-2-hydroxyethyl]amino}-1-(4-fluorobenzoyl)piperidine;
4-{[2-(1,4-benzodioxan-2-yl)-2-hydroxyethyl]amino}-1-(4-trifluoromethylbenzoyl)piperidine;
4-{[2-(1,4-benzodioxan-2-yl)-2-hydroxyethyl]amino}-1-(2,6-dimethylbenzoyl)piperidine;
4-{[2-(1,4-benzodioxan-2-yl)-2-hydroxyethyl]amino}-1-(2,6-dimethoxybenzoyl)piperidine;
4-{[2-(1,4-benzodioxan-2-yl)-2-hydroxyethyl]amino}-1-(3,4-methylenedioxybenzoyl)piperidine;
4-{[2-(1,4-benzodioxan-2-yl)-2-hydroxyethyl]amino}-1-(2,6-dichlorobenzoyl)piperidine;
4-{[2-(1,4-benzodioxan-2-yl)-2-hydroxyethyl]amino}-1-(3,4,5-trimethoxybenzoyl)piperidine;
4-{[2-(1,4-benzodioxan-2-yl)-2-hydroxyethyl]amino}-1-(2-phenylacetyl)piperidine;
4-{[2-(1,4-benzodioxan-2-yl)-2-hydroxyethyl]amino}-1-(5-phenyl-n-pentanoyl)piperidine;
4-{[2-(1,4-benzodioxan-2-yl)-2-hydroxyethyl]amino}-1-(acetyl)piperidine;
4-{[2-(1,4-benzodioxan-2-yl)-2-hydroxyethyl]amino}-1-(propionyl)piperidine;
4-{[2-(1,4-benzodioxan-2-yl)-2-hydroxyethyl]amino}-1-(n-butanoyl)piperidine;
4-{[2-(1,4-benzodioxan-2-yl)-2-hydroxyethyl]amino}-1-(isobutanoyl)piperidine;
4-{[2-(1,4-benzodioxan-2-yl)-2-hydroxyethyl]amino}-1-(n-pentanoyl)piperidine;
4-{[2-(1,4-benzodioxan-2-yl)-2-hydroxyethyl]amino}-1-(cyclopropylcarbonyl)piperidine;
4-{[2-(1,4-benzodioxan-2-yl)-2-hydroxyethyl]amino}-1-(2-methylcyclopentylcarbonyl)piperidine; or
4-{[2-(1,4-benzodioxan-2-yl)-2-hydroxyethyl]amino}-1-(cyclohexylcarbonyl)piperidine, as the hydrochloride salt.

(c) In a corresponding manner to that described in Subpart (a) of this Example, but substituting a stoichiometrically equivalent amount of d,l-erythro-, d,l-threo-[2-(optionally substituted 1,4-benzodioxan-2-yl)-2-hydroxyethyl]amine or mixtures thereof, for [2-(1,4-benzodioxan-2-yl]-2-hydroxyethyl]amine and 1-(lower alkyl, cycloalkyl or optionally substituted phenyl carbonyl)-4-piperidone; 1-(lower alkyl, cycloalkyl or optionally substituted phenyl oxy carbonyl)-4-piperidone; or 1-(lower alkyl, cycloalkyl or optionally substituted phenyl aminocarbonyl)-4-piperidone for 1-(benzoyl)-4-piperidone, there is obtained the corresponding d,l-erythro, d,l-threo-4-{[2-(optionally substituted 1,4-benzodioxan-2-yl)-2-hydroxyethyl]amino}-1-[(lower alkyl, cycloalkyl or optionally substituted phenyl)carbonyl]-piperidine or mixtures thereof; d,l-erythro, d,l-threo-4-{[2-(optionally substituted 1,4-benzodioxan-2-yl)-2-hydroxyethyl]amino}-1-(lower alkyl, cycloalkyl or optionally substituted phenyl oxy carbonyl)-4-piperidine or mixtures thereof; or d,l-erythro, d,l-threo-4-{[2-(optionally substituted 1,4-benzodioxan-2-yl)-2-hydroxyethyl]amino}-1-(lower alkyl, cycloalkyl or optionally substituted phenyl aminocarbonyl)-4-piperidine, or mixtures thereof respectively.

EXAMPLE 5

Preparation of 4-{[2-(1,4-benzodioxan-2-yl)-2-hydroxyethyl]amino}-1-(phenylaminocarbonyl)piperidine Reaction Sequence 5

(a) To a stirred solution of 1.0 g of [2-(1,4-benzodioxan-2-yl)-2-hydroxyethyl)]amine hydrochloride and 1.2 g of 1-(phenylaminocarbonyl)-4-piperidone in 100 ml of methanol was added 500 mg of sodium cyanoborohydride. The reaction was stirred at ambient temperature and pressure (about 25° C.) for sixteen hours then extracted and isolated as the hydrochloride salt as described in Example 4A, 4-{[2-(1,4-benzodioxan-2-yl)-2-hydroxyethyl]amino}-1-(phenylaminocarbonyl)piperidine.

(b) Similarly proceeding as in Subpart (a) above but substituting a stoichiometrically equivalent amount of
1-[(4-methylphenyl)aminocarbonyl]-4-piperidone;
1-[(4-methoxyphenyl)aminocarbonyl]-4-piperidine;
1-[(4-n-butylphenyl)aminocarbonyl]-4-piperidone;
1-[(4-n-butoxyphenyl)aminocarbonyl]-4-piperidone;
1-[(4-chlorophenyl)aminocarbonyl]-4-piperidone;
1-[(4-trifluoromethylphenyl)aminocarbonyl]-4-piperidone;
1-[(2,6-dimethylphenyl)aminocarbonyl]-4-piperidone;
1-[(2,6-dimethoxyphenyl)aminocarbonyl]-4-piperidone;
1-[(2,6-dichlorophenyl)aminocarbonyl]-4-piperidone;
1-[(3,4,5-trimethoxyphenyl)aminocarbonyl]-4-piperidone;
1-[(cyclohexyl)aminocarbonyl]-4-piperidone;
1-[(isopropyl)aminocarbonyl]-4-piperidone;
1-(ethyloxycarbonyl)-4-piperidone, (from ethyl chloroformate and 4-piperidone);
1-(cyclohexyloxycarbonyl)-4-piperidone, (from cyclohexylchloroformate and 4-piperidone); or
1-(phenyloxycarbonyl)-4-piperidone (from phenylchloroformate and 4-piperidone);
for 1-(phenylaminocarbonyl)-4-piperidone the following compounds are obtained:
4-{[2-(1,4-benzodioxan-2-yl)-2-hydroxyethyl]amino}-1-[(4-methylphenyl)aminocarbonyl]piperidine;
4-{[2-(1,4-benzodioxan-2-yl)-2-hydroxyethyl]amino}-1-[(4-methoxyphenyl)aminocarbonyl]piperidine;
4-{[2-(1,4-benzodioxan-2-yl)-2-hydroxyethyl]amino}-1-[(4-n-butylphenyl)aminocarbonyl]piperidine;
4-{[2-(1,4-benzodioxan-2-yl)-2-hydroxyethyl]amino}-1-[(4-n-butoxyphenyl)aminocarbonyl]piperidine;
4-{[2-(1,4-benzodioxan-2-yl)-2-hydroxyethyl]amino}-1-[(4-chlorophenyl)aminocarbonyl]piperidine;
4-{[2-(1,4-benzodioxan-2-yl)-2-hydroxyethyl]amino}-1-[(4-trifluoromethyl)aminocarbonyl]piperidine;
4-{[2-(1,4-benzodioxan-2-yl)-2-hydroxyethyl]amino}-1-[(2,6-dimethylphenyl)aminocarbonyl]piperidine;
4-{[2-(1,4-benzodioxan-2-yl)-2-hydroxyethyl]amino}-1-[(2,6-dimethoxyphenyl)aminocarbonyl]piperidine;
4-{[2-(1,4-benzodioxan-2-yl)-2-hydroxyethyl]amino}-1-[(2,6-dichlorphenyl)aminocarbonyl]piperidine;
4-{[2-(1,4-benzodioxan-2-yl)-2-hydroxyethyl]amino}-1-[(3,4,5-trimethoxyphenyl)aminocarbonyl]piperidine;
4-{[2-(1,4-benzodioxan-2-yl)-2-hydroxyethyl]amino}-1-[(cyclohexyl)aminocarbonyl]piperidine;
4-{[2-(1,4-benzodioxan-2-yl)-2-hydroxyethyl]amino}-1-[(isopropyl)aminocarbonyl]piperidine;
4-{[2-(1,4-benzodioxan-2-yl)-2-hydroxyethyl]amino}-1-(ethyloxycarbonyl)piperidine;

4-{[2-(1,4-benzodioxan-2-yl)-2-hydroxyethyl]amino}-1-(cyclohexyloxycarbonyl)piperidine; or 4-{[2-(1,4-benzodioxan-2-yl)-2-hydroxyethyl]amino}-(1-phenyloxycarbonyl)piperidine as the hydrochloride salt.

(c) In a corresponding manner to that described in Subpart (a) of this Example, when a stoichiometrically equivalent amount of d,l,-erythro-, d,l-threo-[2-(optionally substituted 1,4-benzodioxan-2-yl)-2-hydroxyethyl]amine (or amine hydrochloride) or mixtures thereof is substituted for [2-(1,4-benzodioxan-2-yl)-2-hydroxyethyl]amine and 1-[(optionally substituted phenyl)aminocarbonyl]-4-piperidone is substituted for 1-(phenylaminocarbonyl)-4-piperidine, there is obtained the corresponding d,l-erythro, d,l-threo 4-{[2-(optionally substituted 1,4-benzodioxan-2-yl)-2-hydroxyethyl]amino}-1-[(optionally substituted phenyl)aminocarbonyl]piperidine or mixtures thereof, respectively.

EXAMPLE 5A (Preparation of Compounds of formula I)

(a) A solution of 0.70 g of 1-[(2,6-dimethylphenyl)aminocarbonylmethyl]-4-aminopiperidine and 0.71 g of the d,l-erythro-2-(1,4-benzodioxan-2-yl)-2-epoxide in 20 ml of toluene and 20 ml of methanol is refluxed for 12 hours. Evaporation and chromatography of the residue on silica gel with 10% methanol-methylene chloride gives 0.5 g of d,l-erythro-4-{[2-(1,4-benzodioxan-2-yl)-2-hydroxyethyl]amino}-1-[(2,6-dimethylphenyl)aminocarbonylmethyl]piperidine which is then dissolved in methanol containing excess hydrochloric acid and precipitated with ether to give the HCl salt.

(b) Similarly, proceeding as in Subpart (a) above, but substituting the appropriate 1-(substituted arylaminocarbonyl)piperidine from Preparation C for 1-[(2,6-dimethylphenyl)aminocarbonylmethyl]piperidine, the following exemplary compounds are prepared as the mono- and dihydrochloride salts:

d,l-erythro-4-{[2-(1,4-benzodioxan-2-yl)-2-hydroxyethyl]amino}-1-(phenylaminocarbonylmethyl)piperidine;

d,l-erythro-4-{[2-(1,4-benzodioxan-2-yl)-2-hydroxyethyl]amino}-1-[(4-chlorophenyl)aminocarbonylmethyl]piperidine;

d,l-erythro-4-{[2-(1,4-benzodioxan-2-yl)-2-hydroxyethyl]amino}-1-[(4-methylphenyl)aminocarbonylmethyl]piperidine;

d,l-erythro-4-{[2-(1,4-benzodioxan-2-yl)-2-hydroxyethyl]amino}-1-[(4-methoxyphenyl)aminocarbonylmethyl]piperidine;

d,l-erythro-4-{[2-(1,4-benzodioxan-2-yl)-2-hydroxyethyl]amino}-1-[(4-chlorophenyl)aminocarbonylmethyl]piperidine; or d,l-erythro-4-{[2-(1,4-benzodioxan-2-yl)-2-hydroxyethyl]amino}-1-[(3-chlorophenyl)aminocarbonylmethyl]piperidine.

EXAMPLE 6

Preparation of Salts of Compounds of formula I (a) A solution of 0.70 g of 1-[2,6-dimethylphenyl)aminocarbonylmethyl]piperidine and 0.71 g of the [2-(1,4-benzodioxan-2-yl)-2-hydroxyethyl]amine and 0.80 g of sodium cyanoborohydride in 20 ml of methanol is stirred at ambient temperature and pressure for 12 hours. After a workup of the crude product as described in the above Examples, evaporation and chromatography of the residue on silica gel with 10% methanol-methylene chloride gives 0.5 g of 4-{[2-(1,4-benzodioxan-2-yl)-2-hydroxyethyl]-amino}-1-[(2,6-dimethylphenyl)aminocarbonylmethyl]piperidine which is then dissolved in methanol containing excess HCl and precipitated with ether to give the di-HCl salt.

(b) Similarly, proceeding as in Subpart (a) above, but substituting a stoichiometrically equivalent amount of the appropriate 1-(optionally substituted phenylaminocarbonyl)piperidone from Preparation C for [(2,6-dimethylphenyl)aminocarbonylmethyl]piperidone, the exemplary compounds are prepared as the dihydrochloride salts.

EXAMPLE 7

(a) Similarly, the compounds of formula I produced using any of the procedures of Examples 1, 2, 2A, 3, 4, 4A, or 5 above, may be prepared as the monohydrochloride or, in some cases, the dihydrochloride salts or mixtures thereof using the procedure of Examples 5A or 6.

4-{[2-(1,4-benzodioxan-2-yl)-2-hydroxyethyl]amino}-1-(phenylaminocarbonylmethyl)piperidine mono- or dihydrochloride;

4-{[2-(1,4-benzodioxan-2-yl)-2-hydroxyethyl]amino}-1-[(4-chlorophenyl)aminocarbonylmethyl]piperidine mono- or dihydrochloride;

4-{[2-(1,4-benzodioxan-2-yl)-2-hydroxyethyl]amino}-1-[(4-methylphenyl)aminocarbonylmetyl]piperidine mono- or dihydrochloride;

4-{[2-(1,4-benzodioxan-2-yl)-2-hydroxyethyl]amino}-1-[(4-methoxyphenyl)aminocarbonylmethyl]piperidine mono- or dihydrochloride;

4-{[2-(1,4-benzodioxan-2-yl)-2-hydroxyethyl]amino}-1-[(2,6-dichlorophenyl)aminocarbonylmethyl]piperidine mono- or dihydrochloride,;

4-{[2-(1,4-benzodioxan-2-yl)-2-hydroxyethyl]amino}-1-[(2,6-dimethylphenyl)aminocarbonylmethyl]piperidine mono- or dihydrochloride salt,;

4-{[2-(1,4-benzodioxan-2-yl)-2-hydroxyethyl]amino}-1-[(3,4,5-trimethoxyphenyl)aminocarbonylmethyl]piperidine mono- or dihydrochloride;

4-{[2-(1,4-benzodioxan-2-yl)-2-hydroxyethyl]amino}-1-[(2-chloro-5-methylphenyl)aminocarbonylmethyl]piperidine mono- or dihydrochloride;

4-{[2-(1,4-benzodioxan-2-yl)-2-hydroxyethyl]amino}-1-[(4-thiometylphenyl)aminocarbonylmethyl]piperidinemono- or dihydrochloride;

4-{[2-(1,4-benzodioxan-2-yl)-2-hydroxyetyl]amino}-1-[(4-n-propylsulfinylphenyl)aminocarbonylmethyl]piperidine mono- or dihydrochloride;

4-{[2-[6-chloro-1,4-benzodioxan-2-yl)-2-hydroxyethyl]amino}-1-[(3,5-difluorophenyl)aminocarbonylmethyl]piperidine mono- or dihydrochloride;

4-{[2-(7-ethyl-1,4-benzodioxan-2-yl)-2-hydroxyethyl]amino}-1-[phenylaminocarbonylmethyl]piperidine mono- or dihydrochloride;

4-{[2-(1,4-benzodioxan-2-yl)-2-hydroxyethyl]amino}-1-[(2,6-diethoxyphenyl)aminocarbonylmethyl]piperidine mono- or dihydrochloride;

4-{[2-(1,4-benzodioxan-2-yl)-2-hydroxyethyl]amino}-1-[(3-bromoamino-1-ethylphenyl)aminocarbonylmethyl]piperidine mono- or dihydrochloride;

4-{[2-(6-methoxy-1,4-benzodioxan-2-yl)-2-hydroxyethyl]amino}-1-(phenylaminocarbonylmethyl)piperidine mono- or dihydrochloride;

4-{[2-(5-n-butyl-1,4-benzodioxan-2-yl)-2-hydroxyethyl]}-4-[phenylaminocarbonylmethyl]piperidine mono- or dihydrochloride;

4-{[2-(1,4-benzodioxan-2-yl)-2-hydroxyethyl]amino}-1-[N-methyl-N-(2,6-diethoxyphenyl)aminocarbonylmethyl]piperidine mono- or dihydrochloride; or 4-{[2-(1,4-benzodioxan-2-yl)-2-hydroxyethyl]amino}-1-[4-methylthiophenyl)aminocarbonylmethyl]piperidine mono- or dihydrochloride.

If desired, preceding the exemplary compounds and salts may be converted into the free base form by the procedure in Examples 9 and 11 or to another salt by following the procedure of Example 10.

(b) Similarly, proceeding as in Subpart (a) above, but substituting an equivalent amount of d,l-erythro- or d,l-threo-2-(optionally substituted-1,4-benzodioxan-2-yl)-2-epoxide for 2-(1,4-benzodioxan-2-yl)-2-epoxide, there is obtained the corresponding salt derivatives having the d,l-erythro- or d,l-threo-orientation, respectively.

Exemplary compounds comprise the following:

4-{[2-(1,4-benzodioxan-2-yl)-2-hydroxyethyl]amino}-1-(phenylaminocarbonylmethyl)piperidine mono- or dihydrochloride (d,l-erythro-di-HCl, mp 110°–114° C.);

4-{[2-(1,4-benzodioxan-2-yl)-2-hydroxyethyl]amino}-1-[(4-chlorophenyl)aminocarbonylmethyl]piperidine mono- or dihydrochloride, (d,l-erythro-di-HCl, mp 256°–258° C.);

4-{[2-(1,4-benzodioxan-2-yl)-2-hydroxyethyl]amino}-1-[(4-methoxyphenyl)aminocarbonylmethyl]piperidine mono- or dihydrochloride, (d,l-erythro-di-HCl, mp 169°–170° C.);

4-{[2-(1,4-benzodioxan-2-yl)-2-hydroxyethyl]amino}-1-[(2,6-dichlorophenyl)aminocarbonylmethyl]piperidine mono- or dihydrochloride, (d,l-erythro-di-HCl, mp 166°–170° C.);

4-{[2-(1,4-benzodioxan-2-yl)-2-hydroxyethyl]amino}-1-[(2,6-dimethylphenyl)aminocarbonylmethyl]piperidine mono- or dihydrochloride salt, (d,l-erythro-di-HCl, mp 158°–160° C.);

4-{[2-(1,4-benzodioxan-2-yl)-2-hydroxyethyl]amino}-1-[(2,6-dimethylphenyl)aminocarbonylmethyl]piperidine mono- or dihydrochloride (d,l-threo-di-HCl, mp 196°–199° C.);

4-{[2-(1,4-benzodioxan-2-yl)-2-hydroxyethyl]amino}-1-[(3-trifluoromethylphenyl)aminocarbonylmethyl]piperidine mono- or dihydrochloride, (d,l-erythro-di-HCl, 232°–233° C.);

4-{[2-(1,4-benzodioxan-2-yl)-2-hydroxyethyl]amino}-1-[(4-trifluoromethylphenyl)aminocarbonylmethyl]piperidine mono- or dihydrochloride, (d,l-erythro-di-HCl, 272°–233° C.);

4-{[2-(1,4-benzodioxan-2-yl)-2-hydroxyethyl]amino}-1-[(4-fluorophenyl)aminocarbonylmethyl]piperidine mono- or dihydrochloride, (d,l-erythro-di-HCl, mp 224°–225° C.);

4-{[2-(1,4-benzodioxan-2-yl)-2-hydroxyethyl]amino}-1-[(2-methylthiophenyl)aminocarbonylmethyl]piperidine mono- or dihydrochloride, (d,l-erythro-di-HCl, mp 141°–142° C.);

4-{[2-(1,4-benzodioxan-2-yl)-2-hydroxyethyl]amino}-1-[(4-n-butylphenyl)aminocarbonylmethyl]piperidine mono- or dihydrochloride, (d,l-erythro-di-HCl, 239°–240° C.);

4-{[2-(1,4-benzodioxan-2-yl)-2-hydroxyethyl]amino}-1-[(4-hydroxyphenyl)aminocarbonylmethyl]piperidine mono- or dihydrochloride, (d,l-erythro-di-HCl, 187°–188° C.);

4-{[2-(1,4-benzodioxan-2-yl)-2-hydroxyethyl]amino}-1-[(3,4-methylenedioxyphenyl)aminocarbonylmethyl]piperidine mono- or dihydrochloride, (d,l-erythro-di-HCl, mp 198°–200° C.);

4-{[2-(1,4-benzodioxan-2-yl)-2-hydroxyethyl]amino}-1-[(4-aminosulfonylphenyl)aminocarbonylmethyl]piperidine mono- or dihydrochloride, (d,l-erythro-di-HCl, mp 255°–258° C.);

4-{[2-(1,4-benzodioxan-2-yl)-2-hydroxyethyl]amino}-1-[iso-propylaminocarbonylmethyl]piperidine mono- or dihydrochloride, (d,l-erythro-di-HCl, mp 150° C.);

4-{[2-(1,4-benzodioxan-2-yl)-2-hydroxyethyl]amino}-1-[cyclohexylaminocarbonylmethyl]piperidine mono- or dihydrochloride, (d,l-erythro-di-HCl, mp 178°–180° C.);

4-{[2-(1,4-benzodioxan-2-yl)-2-hydroxyethyl]amino}-1-[phenylaminocarbonyl]piperidine mono- or dihydrochloride, (d,l-erythro-mono-HCl, mp 226°–228° C.);

4-{[2-(1,4-benzodioxan-2-yl)-2-hydroxyethyl]amino}-1-(isopropylaminocarbonyl)piperidine mono- or dihydrochloride, (d,l-erythro-mono-HCl, mp 181°–183° C.);

4-{[2-(1,4-benzodioxan-2-yl)-2-hydroxyethyl]amino}-1-(acetyl)piperidine mono- or dihydrochloride, (d,l-erythro-mono-HCl, mp 126°–129° C.);

4-{[2-(1,4-benzodioxan-2-yl)-2-hydroxyethyl]amino}-1-(phenylcarbonyl)piperidine mono- or dihydrochloride, (d,l-erythro-mono-HCl, mp 221°–222° C.);

4-{[2-(1,4-benzodioxan-2-yl)-2-hydroxyethyl]amino}-1-[(4-fluorophenyl)carbonyl]piperidine mono- or dihydrochloride, (d,l-erythro-mono-HCl, mp 193°–194° C.);

4-{[2-(1,4-benzodioxan-2-yl)-2-hydroxyethyl]amino}-1-[(3,4-methylenedioxyphenyl)carbonyl]piperidine mono- or dihydrochloride, (d,l-erythro-mono-HCl, mp 226°–228° C.); or 4-{[2-(1,4-benzodioxan-2-yl)-2-hydroxyethyl]amino}-1-(3,4,5-trimethoxypropenoyl)piperidine mono- or dihydrochloride, (d,l-erythro-mono-HCl, mp 201°–202° C.).

(c) Similarly, proceeding as in Subpart (a) above, but substituting an equivalent amount of substituted d,l-erythro- or d,l-threo-2-(1,4-benzodioxan-2-yl)-2-epoxide for d,l-threo-2-(1,4-benzodioxan-2-yl)-2-epoxide, there is obtained the corresponding salt derivatives having the corresponding threo-orientation, respectively. The erythro and threo epoxides are described in U.S. Pat. No. 4,212,808.

EXAMPLE 8

Conversion of Free Base to Salt 8.0 g of 4-{[2-(1,4-benzodioxan-2-yl)-2-hydroxyethyl]amino}-[(2,6-dimethylphenyl)aminocarbonylmethyl]piperidine is dissolved in methanol and acidified with methanolic hydrochloric acid. The precipitate is washed with ether to give 7.0 g of the dihydrochloride salt of 4-{[2-(1,4-benzodioxan-2-yl)-2-hydroxyethyl]amino}-1-[(2,6-dimethylphenyl)aminocarbonylmethyl]piperidine.

In similar manner, all compounds of formula I in base form prepared in accordance with Examples 1 to 5 can be converted to the corresponding pharmaceutically acceptable acid addition salts by treatment with the appropriate acid, for example, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

EXAMPLE 9

Conversion of Salt to Free Base 1.0 g of 4-{[2-(1,4-benzodioxan-2-yl)-2-hydroxyethyl]amino}-1-[(2,6-dimethylphenyl)aminocarbonylmethyl]piperidine 2HCl suspended in 50 ml of ether is stirred with excess dilute aqueous potassium carbonate solution until the salt is completely dissolved. The organic layer is then separated, washed twice with water, dried over magnesium sulfate and evaporated to yield 4-{[2-(1,4-benzodioxan-2-yl)-2-hydroxyethyl]amino}-1-[(2,6-dimethylphenyl)aminocarbonylmethyl]piperidine as the free base.

In a similar manner, the acid addition salts prepared in accordance with Example 8 are converted to the corresponding free base.

EXAMPLE 10

Direct Interchange of Acid Addition Salts

4-{[2-(1,4-benzodioxan-2-yl)-2-hydroxyethyl]amino}-1-[(2,6-dimethylphenyl)aminocarbonylmethyl]piperidine acetate (1.0 g) is dissolved in 50 ml 50% aqueous sulfuric acid, and the solution evaporated to dryness. The product is suspended in ethanol and filtered, air dried and recrystallized from methanol/acetone to yield 4-{[2-(1,4-benzodioxan-2-yl)-2-hydroxyethyl]amino}-1-[(2,6-dimethylphenyl)aminocarbonylmethyl]-piperidine.$2HSO_4$.

EXAMPLE 11

Conversion of Salt to Free Base

A solution of 3.5 g of 4-{[2-(1,4-benzodioxan-2-yl)-2-hydroxyethyl]amino}-1-[(2,6-dimethylphenyl)aminocarbonylmethyl]piperidine dihydrochloride salt in water (50 ml) is adjusted to pH 12 with ammonium hydroxide solution and extracted with methylene chloride. The methylene chloride is evaporated to afford 3 g of 4-{[2-(1,4-benzodioxan-2-yl)-2-hydroxyethyl]amino}-[(2,6-dimethylphenyl)aminocarbonylmethyl]-piperidine as the free base.

In a similar manner, the acid addition salts prepared in accordance with Example 8 are converted to the corresponding free base.

EXAMPLE 12

The following example illustrates the preparation of representative pharmaceutical formulations containing an active compound of formula I, e.g., 4-{[2-(1,4-benzodioxan-2-yl)-2-hydroxyethyl]amino}-1-[(2,6-dimethylphenyl)aminocarbonylmethyl]piperidine.

| I.V. Formulation | |
|---|---|
| Active compound | 0.14 g |
| Propylene glycol | 20.0 g |
| POLYETHYLENE GLYCOL 400 | 20.0 g |
| TWEEN 80 | 1.0 g |
| 0.9% Saline solution | 100.0 ml |

In Examples 13 through 19, the active ingredient is 4-{[2-(1,4-benzodioxan-2-yl)-2-hydroxyethyl]amino}-1-[(2,6-dimethylphenyl)aminocarbonylmethyl]piperidine dihydrochloride. Other compounds of formula I and the pharmaceutically acceptable salts thereof may be substituted therein.

EXAMPLE 13

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 14

| Ingredients | Quantity per capsule, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 15

| Ingredients | Quantity per tablet, mgs. |
|---|---|
| Active ingredient | 1 |
| cornstarch | 50 |
| lactose | 145 |
| magnesium stearate | 5 |

The above ingredients are mixed intimately and pressed into single scored tablets.

EXAMPLE 16

| Ingredients | Quantity per capsule, mgs. |
|---|---|
| Active ingredient | 108 |
| lactose | 15 |
| cornstarch | 25 |
| magnesium stearate | 2 |

The above ingredients are mixed and introduced into a hard-shell gelatin capsule.

EXAMPLE 17

| Ingredients | Quantity per tablet, mgs. |
|---|---|
| Active ingredient | 150 |
| lactose | 92 |

The above ingredients are mixed and introduced into a hard-shell gelatin tablet.

EXAMPLE 18

An injectable preparation buffered to a pH of 7 is prepared having the following composition:

| Ingredients | |
|---|---|
| Active ingredient | 0.2 g |
| $KH_2PO_4$ buffer (0.4 M solution) | 2 ml |
| KOH (1 N) | q.s. to pH 7 |

-continued

| Ingredients | |
|---|---|
| water (distilled, sterile) | q.s. to 20 ml |

EXAMPLE 19

An oral suspension is prepared having the following composition:

| Ingredients | | |
|---|---|---|
| Active ingredient | 0.1 | g |
| fumaric acid | 0.5 | g |
| sodium chloride | 2.0 | g |
| methyl paraben | 0.1 | g |
| granulated sugar | 25.5 | g |
| sorbitol (70% solution) | 12.85 | g |
| Veegum K (Vanderbilt Co.) | 1.0 | g |
| flavoring | 0.035 | ml |
| colorings | 0.5 | mg |
| distilled water | q.s. to 100 | ml |

While the present invention has been described with reference to the specific embodiments thereof, it should be understood by those skilled in this art that various changes may be made and equivalents may be substituted without departing from the true spirit and scope of the invention. In addition, many modifications may be made to adopt a particular situation, material, or composition of matter, process, process step or steps, or the present objective to the spirit and scope of the invention. In addition, many modifications may be made to adopt a particular situation, material, or composition of matter, process, process step or steps, or the present objective to the spirit of this invention without departing from its essential techings.

What is claimed is:

1. A compound of the formula:

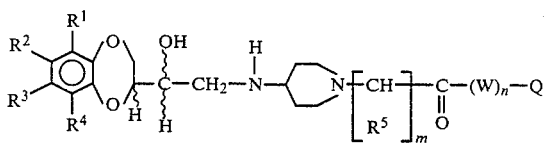

or a pharmaceutically acceptable acid addition salt thereof, wherein:

$R^1$, $R^2$, $R^3$ and $R^4$ are each independently hydrogen, lower alkyl, lower alkoxy, trifluoromethyl, halo, lower alkylthio, lower alkyl sulfinyl or lower alkyl sulfonyl;

$R^5$ is hydrogen or lower alkyl;

m is 0 or 1;

W is alkylene, —CH=CH—, —O—, or —N($R^6$)—, where $R^6$ is lower alkyl or hydrogen;

n is 0 or 1; and

Q is lower alkyl, cycloalkyl of 3-8 carbon atoms or optionally substituted phenyl of the formula

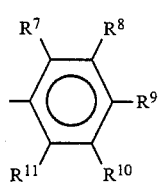

wherein each of $R^7$, $R^8$, $R^9$, $R^{10}$ and $R^{11}$ is independently chosen from hydrogen, lower alkyl, lower alkoxy, trifluoromethyl, halo, lower alkylthio, lower alkyl sulfinyl or lower alkyl sulfonyl, aminosulfonyl or hydroxyl or $R^8$ and $R^9$ together form a —OCH$_2$O— linkage.

2. The compound of claim 1 wherein two substituents of $R^1$, $R^2$, $R^3$ or $R^4$ are hydrogen.

3. The compound of claim 1 wherein $R^1$, $R^2$, $R^3$ and $R^4$ are each hydrogen.

4. The compound of claim 3 wherein m is 1 and $R^5$ is hydrogen.

5. The compound of claim 4 wherein n is 1.

6. The compound of claim 5 wherein W is —N($R^6$)— and $R^6$ is hydrogen.

7. The compound of claim 6 wherein Q is optionally substituted phenyl of the formula:

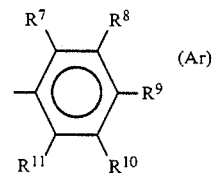

8. The compound of claim 7 wherein three substituents of $R^7$, $R^8$, $R^9$, $R^{10}$ and $R^{11}$ are hydrogen.

9. The compound of claim 8 wherein Q is 2,6-dimethylphenyl, i.e., 4-{[2-(1,4-benzodioxan-2-yl)-2-hydroxyethyl]amino}-1-[(2,6-dimethylphenyl)aminocarbonylmethyl]piperidine, or a pharmaceutically acceptable acid addition salt thereof.

10. The compound of claim 8 wherein Q is 3,4-methylenedioxyphenyl, i.e., 4-{[2-(1,4-benzodioxan-2-yl)-2hydroxyethyl]amino}-1-(3,4-methylenedioxyphenyl)aminocarbonylmethyl]piperidine, and the pharmaceutically acceptable salts thereof.

11. The compound of claim 8 wherein Q is 2,6-dichlorophenyl, i.e., 4-{[2-(1,4-benzodioxan-2-yl)-2-hydroxyethyl]amino}-1-[(2,6-dichlorophenyl)aminocarbonylmethyl]piperidine, and the pharmaceutically acceptable acid addition salts thereof.

12. The compound of claim 7 wherein four substituents of $R^7$, $R^8$, $R^9$, $R^{10}$ or $R^{11}$ are hydrogen.

13. The compound of claim 12 wherein Q is 4-methylphenyl, i.e., 4-{[2-(1,4-benzodioxan-2-yl)-2-hydroxyethyl]amino}-1-[(4-methylphenyl)aminocarbonylmethyl]piperidine, or a pharmaceutically acceptable acid addition salt thereof.

14. The compound of claim 12 wherein Q is 3-methylthiophenyl, i.e., 4-{[2-(1,4-benzodioxan-2-yl)-2-hydroxyethyl]amino}-1-[(4-methylthiophenyl)aminocarbonyl-1-methyl)]piperidine, or a pharmaceutically acceptable acid addition salt thereof.

15. The compound of claim 12 wherein Q is 4-n-butylphenyl, i.e. 4-{[2-(1,4-benzodioxan-2-yl)-2-hydroxyethyl]amino}-1-[(4-n-butylphenyl)aminocarbonylmethyl]piperidine, or a pharmaceutically acceptable acid addition salt thereof.

16. The compound of claim 12 wherein Q is 4-fluorophenyl, i.e., 4-{[2-(1,4-benzodioxan-2-yl)-2-hydroxyethyl]amino}-1-[(4-fluorophenyl)aminocarbonylmethyl]piperidine, or a pharmaceutically acceptable acid addition salt thereof.

17. The compound of claim 12 wherein Q is 4-chlorophenyl, i.e. 4-{[2-(1,4-benzodioxan-2-yl)-2-hydroxyethyl]amino}-1-[(4-chlorophenyl)aminocarbonylmethyl]piperidine, or a pharmaceutically acceptable acid addition salt thereof.

18. The compound of claim 12 wherein Q is 3-trifluoromethylphenyl, i.e., 4-{[2-(1,4-benzodioxan-2-yl)-2-hydroxyethyl]amino}-1-[(3-trifluoromethylphenyl)aminocarbonylmethyl]piperidine, or a pharmaceutically acceptable acid addition salt thereof.

19. The compound of claim 12 wherein Q is 4-trifluoromethylphenyl, i.e. 4-{[2-(1,4-benzodioxan-2-yl)-2-hydroxyethyl]amino}-1-[(4-trifluoromethylphenyl)aminocarbonylmethyl]piperidine, or a pharmaceutically acceptable acid addition salt thereof.

20. The compound of claim 12 wherein Q is 4-methoxyphenyl, i.e., 4-{[2-(1,4-benzodioxan-2-yl)-2-hydroxyethyl]amino}-4-[(4-methoxyphenyl)aminocarbonylmethyl]piperidine, or a pharmaceutically acceptable acid addition salt thereof.

21. The compound of claim 12 wherein Q is 4-hydroxyphenyl, i.e., 4-{[(1,4-benzodioxan-2-yl)-2-hydroxyethyl]amino}-1-[(4-hydroxyphenyl)aminocarbonylmethyl]piperidine, or a pharmaceutically acceptable acid addition salt thereof.

22. The compound of claim 12 wherein Q is 4-aminosulfonylphenyl, i.e., 4-{[2-(1,4-benzodioxan-2-yl)-2-hydroxyethyl]amino}-1-[(4-aminosulfonylphenyl)aminocarbonylmethyl)]piperidine, or a pharmaceutically acceptable acid addition salt thereof.

23. The compound of claim 7 wherein Q is phenyl, i.e., 4-{[2-(1,4-benzodioxan-2-yl)-2-hydroxyethyl]amino}-1-(phenylaminocarbonylmethyl)piperidine, or a pharmaceutically acceptable acid addition salt thereof.

24. The compound of claim 3 wherein m is 0, W is —N(R)$^6$—, and n is 1.

25. The compound of claim 24 wherein R$^6$ is hydrogen.

26. The compound of claim 25 wherein Q is phenyl, i.e., 4-{[2-(1,4-benzodioxan-2-yl)-2-hydroxyethyl]amino}-1-[(phenyl)aminocarbonyl]piperidine, or a pharmaceutically acceptable acid addition salt thereof.

27. The compound of claim 25 wherein Q is isopropyl, i.e. 4-{[2-(1,4-benzodioxan-2-yl)-2-hydroxyethyl]amino}-1-[isopropylaminocarbonyl]piperidine, or a pharmaceutically acceptable acid addition salt thereof.

28. The compound of claim 25 wherein Q is cyclohexyl, i.e., 4-{[2-(1,4-benzodioxan-2-yl)-2-hydroxyethyl]amino}-1-[cyclohexylaminocarbonyl]piperidine, or a pharmaceutically acceptable acid addition salt thereof.

29. The compound of claim 3 wherein m and n are each 0.

30. The compound of claim 29 wherein Q is phenyl, i.e., 4-{[2-(1,4-benzodioxan-2-yl)-2-hydroxyethyl]amino}-1-(benzoyl)piperidine, or a pharmaceutically acceptable acid addition salt thereof.

31. The compound of claim 29 wherein Q is 4-fluorophenyl, i.e., 4-{[2-(1,4-benzodioxan-2-yl)-2-hydroxyethyl]amino}-1-(4-fluorobenzoyl)piperidine, or a pharmaceutically acceptable acid addition salt thereof.

32. The compound of claim 29 wherein Q is 3,4-methylenedioxyphenyl, i.e. 4-{[2-(1,4-benzodioxan-2-yl)-2-hydroxyethyl]amino}-1-(3,4-methylenedioxybenzoyl)piperidine, or a pharmaceutically acceptable acid addition salt thereof.

33. The compound of claim 29 wherein Q is methyl, i.e., 4-{[2-(1,4-benzodioxan-2-yl)-2-hydroxyethyl]amino}-1-(methylcarbonyl)piperidine, or a pharmaceutically acceptable acid addition salt thereof.

34. The compound of claim 3 wherein m is 0, W is —CH=CH— and n is 1.

35. The compound of claim 34 wherein Q is 3,4,5-trimethoxyphenyl, i.e., 4-{[2-(1,4-benzodioxan-2-yl)-2-hydroxyethyl]amino}-1-[3-(3,4,5-trimethoxyphenyl)propenoyl]piperidine, or a pharmaceutically acceptable acid addition salt thereof.

36. A pharmaceutical composition useful for treating a cardiovascular disease in a mammal which comprises a therapeutically effective amount of a compound of claim 1 in admixture with a pharmaceutically acceptable excipient.

37. A pharmaceutical composition of claim 36 wherein said mammal is a human being.

38. A pharmaceutical composition useful for treating an autoimmune disease in a mammal which comprises a therapeutically effective amount of a compound of claim 1 in admixture with a pharmaceutically acceptable excipient.

39. A pharmaceutical composition of claim 36 wherein said mammal is a human being.

40. A method for treating a cardiovascular disease in a mammal which method comprises administering to a subject in need of such treatment a therapeutically effective amount of the compound of claim 1.

41. A method of claim 40 wherein said mammal is a human being.

42. The method of claim 41 wherein said cardiovascular disease is myocardial infarction.

43. The method of claim 41 wherein said cardiovascular disease is variant angina.

44. The method of claim 41 wherein said cardiovascular disease is exercise-induced angina.

45. The method of claim 41 wherein said cardiovascular disease is hypertension.

46. The method of claim 41 wherein said cardiovascular disease is arrhythmia.

47. A method for treating an autoimmune disease in a mammal which method comprises administering to a subject in need of such treatment a therapeutically effective amount of the compound of claim 1.

48. A method of claim 47 wherein said mammal is a human being.

49. The method of claim 47 wherein said autoimmune disease is rheumatoid arthritis.

* * * * *